US012168010B2

(12) United States Patent
Coy et al.

(10) Patent No.: US 12,168,010 B2
(45) Date of Patent: Dec. 17, 2024

(54) USE OF CO-ENZYME ANTAGONISTS TO SLOW METABOLISM

(71) Applicant: Tavargenix GmbH, Darmstadt (DE)

(72) Inventors: Johannes Coy, Hainburg (DE); Ralf Schierl, Darmstadt-Eberstadt (DE)

(73) Assignee: Tavargenix GmbH, Darmstadt (DE)

( * ) Notice: Subject to any disclaimer, the term of this patent is extended or adjusted under 35 U.S.C. 154(b) by 0 days.

(21) Appl. No.: 18/010,816

(22) PCT Filed: Jun. 21, 2021

(86) PCT No.: PCT/DE2021/100528
§ 371 (c)(1),
(2) Date: Dec. 16, 2022

(87) PCT Pub. No.: WO2021/259423
PCT Pub. Date: Dec. 30, 2021

(65) Prior Publication Data
US 2023/0226060 A1   Jul. 20, 2023

(30) Foreign Application Priority Data
Jun. 27, 2020   (DE) ..................... 10 2020 116 980.9

(51) Int. Cl.
| A61K 31/51 | (2006.01) |
| A61K 45/06 | (2006.01) |
| A61P 31/12 | (2006.01) |
| A61P 35/00 | (2006.01) |

(52) U.S. Cl.
CPC .............. *A61K 31/51* (2013.01); *A61K 45/06* (2013.01); *A61P 31/12* (2018.01); *A61P 35/00* (2018.01)

(58) Field of Classification Search
CPC ................................. A61K 31/51; A61P 35/00
See application file for complete search history.

(56) References Cited

U.S. PATENT DOCUMENTS

| 11,236,381 B2* | 2/2022 | Coy ........................... A61P 9/10 |
| 2002/0049157 A1 | 4/2002 | Wu et al. |
| 2006/0002922 A1 | 1/2006 | Xu |
| 2009/0209554 A1* | 8/2009 | Boyd .................... C07D 417/14 514/342 |

FOREIGN PATENT DOCUMENTS

| EP | 2256500 B1 * | 4/2014 | ................ A61P 1/04 |
| WO | 2006094716 A1 | 9/2006 | |
| WO | 2020006199 A2 | 1/2020 | |

OTHER PUBLICATIONS

Grimm et al. Clin. Transl. Oncol., 2016, vol. 18, pp. 196-205 (Year: 2016).*
Wang et al. Experimental Hematology & Oncology, 2013, 2:18, pp. 1-14 (Year: 2013).*
Lu et al. Genet. Mol. Res., 2015, vol. 14, No. 3, pp. 11043-11051 (Year: 2015).*
Esteban Elisabeth et al, "Immunomodulation in Sepsis: The Role of Endotoxin Removal by Polymyxin B-Immobilized Cartridge", GB 01., vol. 2013, p. 1-12, URL:http://downloads.hindawi.com/journals/mi/2013/507539.pdf (XP055840784) (Jan. 1, 2013).
Jones J H et al, "Effect of oxythiamine on infection of mice with the Lansing strain of poliomyelitis virus", vol. 69, No. 3 (Jan. 1, 1948).
Choi Eun Jung et al, "Allithiamine Exerts Therapeutic Effects on Sepsis by Modulating Metabolic Flux during Dendritic Cell Activation", Molecules and Cells, vol. 43, No. 11, pp. 964-973 (Nov. 30, 2020).
Coy Johannes, "EDIM-TKTL1/Apo10 Blood Test: An Innate Immune System Based Liquid Biopsy for the Early Detection, Characterization and Targeted Treatment of Cancer", International Journal of Molecular Sciences, vol. 18, No. 4, p. 878 (Apr. 20, 2017).
Michalak et al, Erythrocyte transketolase activity in patients with diabetic and alcoholic neuropathies, Folia Neuropathol 2013; 51(3):222-226 (2013).
Molina Patricia E et al, "Thiamin deficiency impairs endotoxin-induced increases in hepatic glucose output", American Journal of Clinical Nutrition, vol. 59, No. 5, p. 1045-1049 (XP009529981) (1994).
Sassoon Catherine S et al, "Inhibition of Intestinal Thiamin Transport in Rat Model of Sepsis", vol. 44, No. 9 (Aug. 31, 2016).
Siemieniuk et al., Thiamine antivitamins—an opportunity of therapy of fungal infections caused by Malassezia pachydermatis and Candida albicans, Mycoses, vol. 59, p. 108-116 (2016).
Smeets et al, A NADH-dependent transketolase assay in erythrocyte hemolysates'. Clin. Chim. Acta. 33 (2): 379-86 (Jul. 1971).
Takeuchi et al., Improved determination of transketolase activity in erythrocytes. Clinical Chemistry, vol. 30, Issue 5, pp. 658-661 (May 1, 1984).
Tylicki et al, Thiamine and selected thiamine antivitamines—biological activity and methods of synthesis. In: Bioscience Reports 38, p. 1-23 (Jan. 2018).
Von Seth M et al, "P349—Muscle mitochondrial function and N+/K+-Atpase activity are unaffected by sepsis in pigs", Critical Care, vol. 21, No. 1, Supp. 1: . 349 (Mar. 1, 2017).

(Continued)

*Primary Examiner* — James D. Anderson
(74) *Attorney, Agent, or Firm* — Agris & von Natzmer LLP; Joyce von Natzmer

(57) ABSTRACT

The invention relates to the use of at least one inhibitory structural analog or inhibitory functional analog of a coenzyme (such as thiamine for example) of an enzyme group, the enzyme members of which catalyze anabolic and/or catabolic and/or energy-releasing metabolic reactions that are of essential significance for the functionality of the overall metabolism of cells, in particular mammalian cells. The invention is used to treat patients in order to produce a general successive (in particular also continuous) slowing down of the metabolic processes of endogenous cells and exogenous cells in the body of the patient and thus achieve a slowing down of disease-causing processes in particular.

18 Claims, 7 Drawing Sheets

(56) References Cited

OTHER PUBLICATIONS

Wyss, Antibacterial Action of a Pyridine Analogue of Thiamine, Journal of Bacteriology, p. 483-484 (1943).
Abdou E, Hazell AS. Thiamine deficiency: an update of pathophysiologic mechanisms and future therapeutic considerations. Neurochem Res. Feb. 2015;40(2):353-61 (Epub Oct. 9, 2014).
Smith TJ et al., Thiamine deficiency disorders: a clinical perspective. Ann N Y Acad Sci. 2021;1498(1):9-28 (Dec. 10, 2020).
Kollmar R., Therapeutic Hypothermia—Principles, Indications, Practical Application (Abstract Only), Uni-Med Science, 1st edition 2012, Hardcover, ISBN 978-3-8374-1371-7 (Germany), 2012.
Larsen R., Hypothermie. Anästhesie und Intensivmedizin für die Fachpflege (Hypothermia. Anaesthesiology and intensive care medicine for specialist care) Jun. 14, 2016:994-7 (Jul. 14, 2016), English Translation of chapters 71.2.1 and 71.3.1. and 71.3.2, 1st paragr. provided.
Holzer M., Indikationen für die Hypothermie—welche sind gesichert, welche bieten eine Option (Indications for hypothermia—which are certain, which offer an option), Der Notarzt S1: S4-S7 (2015). English Translation first page, col. 1-col. 2 first part provided.
U.S. Department of Health and Human Services, Food and Drug Administration, Center for Drug Evaluation and Research (CDER), Pharmacology and Toxicology: Guidance for Industry, Estimating the Maximum Safe Starting Dose in Initial Clinical Trials for Therapeutics in Adult Healthy Volunteers (Jul. 2005).

\* cited by examiner

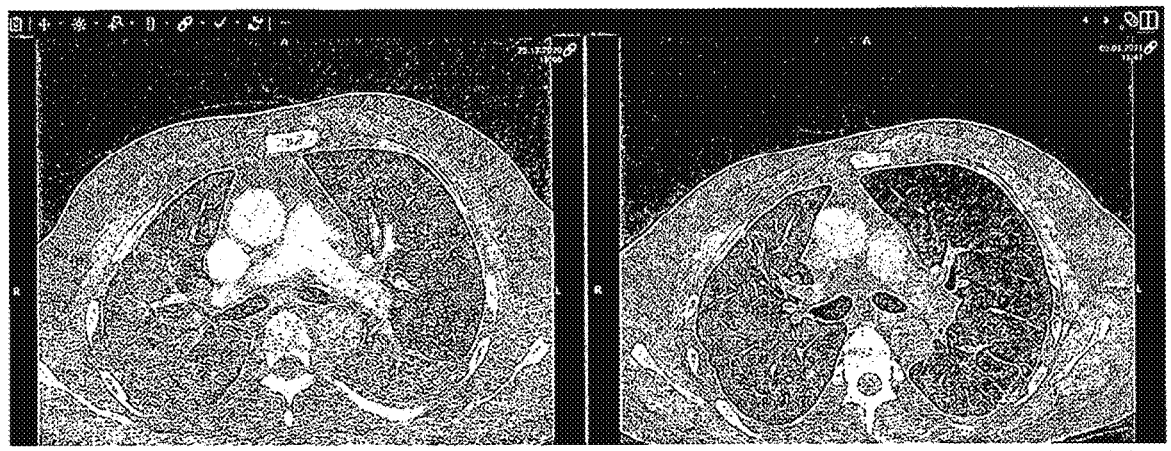
Fig. 3-A　　　　　　　　　　　　　Fig. 3-B
Fig. 4-A　　　　　　　　　　　　　Fig. 4-B
Fig. 5-A　　　　　　　　　　　　　Fig. 5-B

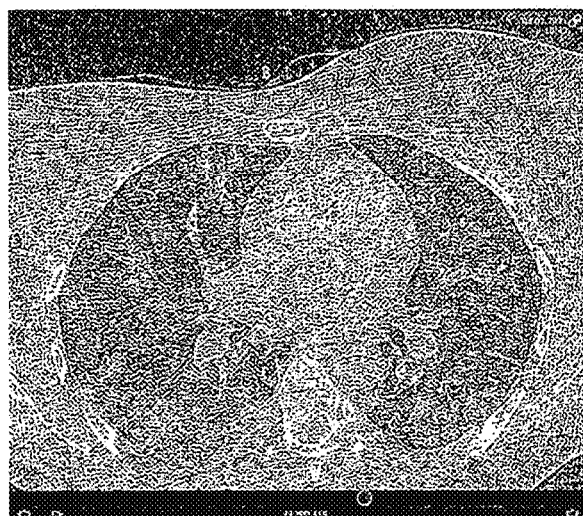
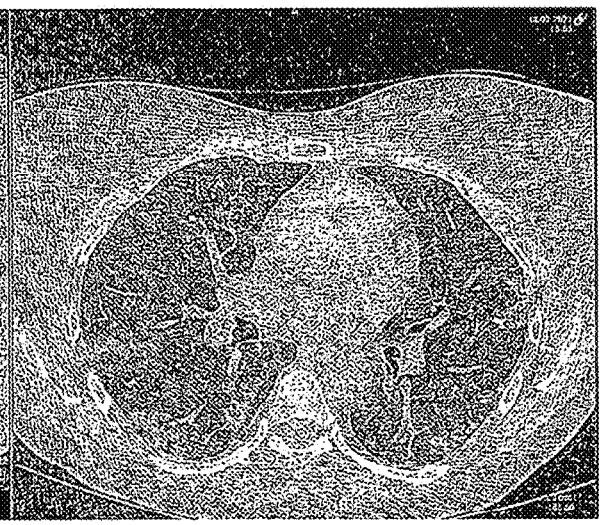
Fig. 6-A　　　　　　　　　　　　　　Fig. 6-B
Fig. 6-C　　　　　　　　　　　　　　Fig. 6-D
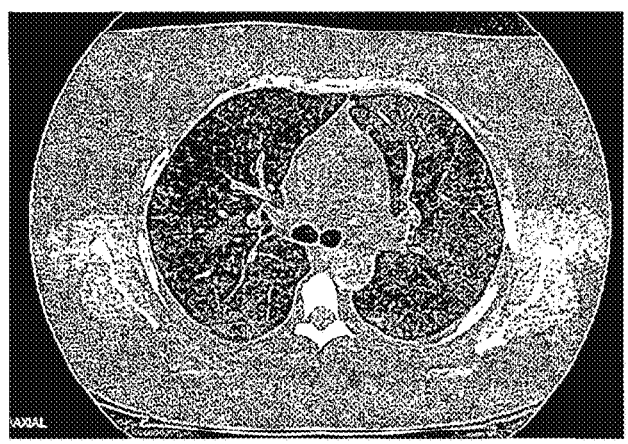
Fig. 7

USE OF CO-ENZYME ANTAGONISTS TO SLOW METABOLISM

CROSS-REFERENCE TO RELATED APPLICATIONS

This is the U.S. national stage of International application PCT/DE2021/100528, filed Jun. 21, 2021 designating the United States and claiming priority to DE 0 2020 116 980.9, filed Jun. 27, 2020.

FIELD OF THE INVENTION

The invention relates to the use of at least one inhibitory structural analog or inhibitory functional analog of a co-enzyme (such as e.g. thiamine) of an enzyme group, the enzyme members of which catalyze anabolic and/or catabolic and/or energy-releasing metabolic reactions of essential importance for the functional capability of the overall metabolism of cells, in particular mammalian cells, for the treatment of patients for the purpose of general successive (in particular also stepless) slowing down of the metabolic processes of endogenous and exogenous cells in the body of the patient.

BACKGROUND OF AND INTRODUCTION TO THE INVENTION

Every illness of a patient is a process. The faster this process runs/progresses, the less time there is for palliative or curative therapies (therapeutic measures/therapeutic interventions). Processes that damage the body can be characterized by the damage that happens in a given unit of time. As a rule, the higher the damage per unit of time, the more serious the overall damage.

In addition to the extent of the processes damaging the body, it is also the speed of the processes damaging the body that determines the severity of the disease and the death of the patient. Often, the speed is even the decisive factor as to whether processes damaging the body are fatal.

In the case of diseases caused by bacteria or viruses, the exponential growth/multiplication of the bacteria or viruses per unit of time is decisive for the severity of the course of the disease. Recurrent examples here are viral diseases that cause influenza or flu-like illnesses or, as most recently, Covid 19 disease, or bacterial infections that cause sepsis. If bacteria or fungi penetrate the bloodstream, they or substances released by them or toxic substances (toxins) can trigger serious illnesses such as blood poisoning, which can be fatal. Most unfortunately, antibiotic therapies that are actually successful in killing the bacteria in the body are sometimes fatal because the toxins (e.g. endotoxins) released during the killing process trigger reactions that can lead to the death of the patient. It is therefore important to consider not only the bacteria-killing effect, but also the consequences of killing of the bacteria. For example, the endotoxin released by killed and then decaying bacteria triggers episodes of fever. Released toxins can ultimately trigger acute sepsis, which leads to organ failure and death of the patient within a short time. Slow processes that drag on for weeks can also lead to septic complications that can cause the patient's death. Therefore, in addition to antibiotic therapy itself, it is useful to take therapeutic measures that address the consequences of antibiotic therapy and the toxin release triggered thereby. The negative consequences of toxin release should be controlled and inhibited in such a way that septic complications or sepsis do not occur, thus saving the patient from serious or/and fatal consequences. If the amount of toxin exceeds a threshold value, the consequences of the toxin effect can no longer be compensated for by the body and the patient dies. Since the amount of toxin in a bacterial infection correlates with the amount of bacteria, bacterial proliferation is largely responsible for the amount of toxin released and is a factor in determining the patient's risk of death due to toxin exposure. A general slowing of bacterial growth in the body is thus a starting point for influencing the amount of toxin and thus the probability of dying from the toxin in such a way that the patient has a higher probability of survival.

Furthermore, antibiotic therapy that successfully kills the bacteria is also the reason for the failure of the therapy, as the toxin levels released by killing the bacteria can lead to septic complications and sepsis. Since toxins such as endotoxin exert their dangerous effects via toll-like receptors and/or inflammatory signaling pathways, inhibition of these toll-like receptors or inflammatory signaling pathways can inhibit the dangerous toxin effect. This makes it possible to make the actual antibiotic therapy safer and more successful by inhibiting the effect of the toxins via inhibition of the associated signaling pathways.

In diseases with immunological and/or excessive inflammatory reactions and inflammatory symptoms and in autoimmune diseases, the proliferation of inflammatory cells and/or cells of the immune system per unit of time is also decisive for the severity of the course of the disease. Practical examples of this are rheumatic attacks in patients with rheumatoid arthritis or recurrent MS attacks in patients with the relapsing-remitting form of multiple sclerosis.

In all these cases, it would help the patient and the treating physicians if the cell proliferation of immune cells that proliferate rapidly or of (almost) all immune cells could be temporarily slowed down to gain time, either for a targeted therapeutic treatment or for mobilizing the patient's own body defenses.

SUMMARY OF THE INVENTION

The present invention is based on the task of satisfying this need.

A solution to this problem is the provision of at least one inhibitory structural analog or inhibitory functional analog of a co-enzyme (such as e g thiamine) of an enzyme group, the enzyme members of which catalyse anabolic and/or catabolic and/or energy-releasing metabolic reactions of essential importance for the functioning of the overall metabolism of mammalian cells, (preferably also of bacterial cells or other organisms present in the organism of a mammal), for use in the treatment of a patient for the purpose of a general successive (in particular also stepless) throttling/slowing down/braking of the anabolic, catabolic and energy-providing metabolic processes of the (i.e. in principle all or almost all) cells in the patient's body (i.e. the body's own cells and also exogenous cells in the patient's body).

On the one hand, this slows down health-preserving and disease-causing processes simultaneously in such a way that a gain in time is generated. In the time gained, the patient organism itself can react to pathogenic processes, and/or the pathogenic processes in the patient's body are slowed down in such a way that the amount of damage per time interval is reduced in such a way that the overall damage to the patient organism is less and/or more time is available for finding therapies with good prospects of success. The time gain can also be used to reduce the effect of therapies and/or their side effects in such a way that the side effects are lower. The latter is particularly advantageous if the therapy is fundamentally successful. For example, if the negative effect of toxins released during the successful killing of bacteria (e.g., endotoxin) is inhibited because signaling pathways that play a role in toxin action are generally inhibited non-specifically by metabolic slowing, the therapy will be even more successful overall. The throttling/slowing down/braking of the metabolic processes also leads to a lowering of the threshold value for cell death.

The slowing down of the cell metabolism can occur up to complete metabolic blockade. The duration and/or amount of the applied active substance must be selected in such a way that most of the healthy cells can reactivate their metabolism after the metabolic slowdown has been lifted and do not suffer any permanent damage, or that the permanent damage is tolerable in view of the success of the therapy.

The term "co-enzyme of an enzyme group" means here in context: all enzymes of this group (the so-called "enzyme members") absolutely require this co-enzyme for the exercise of their catalytic activity; or in other words: for all enzymes of this group, this co-enzyme is essential for the exercise of their catalytic activity.

The term "inhibitory structural analogue" of the co-enzyme—or "co-enzyme antagonist" for short—stands here for a structural analogue of the co-enzyme that binds to the enzyme in question instead of the co-enzyme and inhibits its catalytic activity (the enzyme activity).

The term "inhibitory functional analogue" of the co-enzyme stands here for a substance which, although not having a structure analogous to the co-enzyme, is capable of taking its place in/on the enzyme and/or—due to an interaction with the co-enzyme—functionally inhibiting its action and thus the action of the enzyme in question.

In the following, the term "inhibitory co-enzyme analogue" stands for an inhibitory structural analogue according to the invention and/or an inhibitory functional analogue of a co-enzyme according to the two definitions given above.

In the following, the abbreviation "GSSV" stands for the formulation "general, successive (in particular, if required, also stepless) metabolic slowing down", where metabolic slowing down is to be understood as the slowing down (or throttling or braking) of anabolic, and/or catabolic, and/or energy-providing metabolic processes that are essential for the existence of mammalian cells.

The term "dosage regimen" (synonyms: dosage regimen, administration regimen) used in the following means here in context the planned sequence of individual doses (synonyms: administration quantities, individual administrations) of a drug with specification of the time intervals between the doses, the amount (quantity) of the individual dose to be taken in each case, the duration of the treatment phase(s), and the specification of how and in which formulation (dosage form) the active substance or the drug is to be taken.

The term "targeted cancer therapy" or "targeted therapy" for short is used here in the context of a drug-based cancer therapy in which one or more active substances are administered that are directed at defined tumor-specific target structures of the tumor cells. These defined targets include, for example, receptors or enzymes of the tumor cells. The active agents, which are also referred to here in context as "cell type-specific agents," include, for example, antibodies (e.g., anti-EGFR) or differently designed protein structures (e.g. hormone antagonists or soluble receptors for signaling molecules), hormones, derivatives of hormones, substances that transmit or inhibit signals (e.g. immunomodulatory substances), and so-called "small molecules" (e.g. tyrosine kinase inhibitors such as sorafenib, imatinib, etc.).

The core of the invention is the indication of a completely new way of therapy of diseases, which is characterized by the fact that the metabolism of the diseased person is specifically inhibited and thus slowed down overall in order to slow down processes taking place in the body, which are directly or indirectly damaging. This new form of therapy is referred to below as GSSV therapy.

The use according to the invention and the GSSV (induced) thereby do not distinguish between healthy and degenerated cells, nor between endogenous and exogenous cells in the patient's body. Exogenous cells include in particular prokaryotes such as bacteria, unicellular or multicellular eukaryotes such as fungi, parasitic flagellates or worms, and also infectious organic structures that mammalian cells use for their reproduction, such as RNA viruses or DNA viruses.

Via the dosage regime (time intervals and amount of the administered drug), the strength and duration of the metabolic inhibition can be varied practically at will and in particular also steplessly and can be controlled precisely. This means that the provision of essentially important substrates, which are necessary for downstream specific enzyme reactions, is in principle inhibited in all cells of the patient's body (i.e. both in the healthy and, if present, in the degenerated body cells of the patient's organism as well as in bacterial cells, fungal cells or the cells of parasites or commensals present in the body) over a predetermined limited period of time. This period of time is selected or dimensioned in such a way that no (or only slight) irreversible damaging effects are caused in the body's own healthy cells, and that after termination of the metabolic inhibition (by discontinuation of the drug according to the invention or administration of the functionally active cofactor), especially the healthy body cells of the patient reinforce (ramp up) their metabolism, all enzymatic processes can be carried out again to their full extent and the large majority of the healthy body cells do not suffer (sustain) any permanent damage.

In the course of the experiments underlying this invention, it was surprisingly found that the inhibitory thiamine analogue B-OT exerts the desired effect in dogs and humans in significantly lower concentrations than in rats and mice. If the amounts of B-OT (amount per kilogram of body weight) applied to rats and mice (i.e. rodents) were used in the same way in dogs and humans, the latter reacted much more violently and, under certain circumstances, to an undesirably strong extent, which in many cases led to death. In particular, the surprising discovery underlying this invention is that, compared to the published amounts used in rats and mice (rodents), an approximately two hundredfold lower dose can be used in humans and dogs (non-rodents) to avoid serious, sometimes fatal, courses.

The present invention provides a new tool for protecting against and combating both existing diseases and diseases that may occur in the future and are not currently foreseeable.

The body of a mammal/human ultimately represents a system in which mammalian cells or human cells are in contact with other living beings, and all are in competition for resources such as energy for survival. In this context, the mammalian organism itself represents a resource that is the target of many living beings surrounding it. Especially bacteria, viruses, protozoa and parasites represent living beings or multiplying units within living beings, which either live in peaceful coexistence with the mammalian organism/human organism or cause it health damage up to death. Evolution has led to a constant competition between attackers and defenders, thus triggering a constant improvement of the attackers and the defenders. Losers in this constant race for improvement have become extinct in the course of evolution, so that both today's attackers and today's living defenders are currently in a relatively stable state with respect to each other. From an evolutionary point of view, however, this current stability is very fragile, since no one can predict whether attackers will develop completely new strategies against which defenders will not be able to defend themselves in the future. Currently, the spread of the coronavirus SARS-COV-2 and the disease COVID-19 triggered by it show how attackers can evolve in such a way that they can infect new hosts, spread massively there and trigger novel disease patterns. Many people do not have adequate defenses against such altered attackers, so that they become seriously ill or even die.

With the present invention, it is possible that regardless of the principle of how a new attacker will damage the mammalian/human organism, the effects that such a new pathogen exerts on the organism in question can be slowed down in such a way that the extent of the disease can be selectively, successively and, if necessary, steplessly slowed down and reduced. The time course of the disease is thus stretched out so that the organism (or body) has more time to react to it, and at the same time the extent of the damage per unit of time is reduced. Thus, it is possible to reduce the extent of damage per unit of time so that it can be endured by the body. In other words, if one lengthens the time axis in which the damage acts and simultaneously reduces the damage intensity, it is possible to achieve that the damage is reduced in such a way that it causes less damage to the body as a whole. The amount of damage or damage intensity is reduced in such a way that the body can better tolerate or cope with it.

With this effect of extending the disease over time while reducing the damage, valuable time is gained to be able to test which therapies help the patient. To date, it is often the case that a doctor has to decide within a short time which drug to administer or which therapy to use in the case of very rapid disease progression. The multiplication of bacteria, parasites or viruses in the body of an infected person can proceed in an exponential manner, so that there is extremely little time for decisions. In such cases, there is no way to test another drug or therapy in the patient if the first choice proves ineffective. Slowing down the multiplication of the aggressors (e.g. bacteria, parasites or viruses) in the patient's organism provides the doctor with the necessary time to test out which drug or therapy is effective.

This gain in time to be able to identify effective drugs or effective therapies that work for the patient concerned is a very decisive advantage of the present invention. Since the application according to the invention can be adapted to the individual needs of the patient's organism, it is achieved that it basically works equally well in all patients with the same disease. The slowing down of the patient's metabolism thus offers the possibility of determining at an individual level which drug or which therapy is effective in this patient, i.e. precisely in this individual case.

The gain in time generated by a metabolic slowdown also provides the crucial advantage of giving the body and its defense mechanisms, such as the immune system, more time to find the right defense against external invaders. For example, the formation of antibodies by the human immune system is a stochastic process in which new antibody variants are formed by random recombinations of corresponding genes. Testing of the antibodies then determines which of the antibodies the body produces to fight off the external invader or to eliminate the unwanted endogenous cell, e.g. tumor cell. Since the random formation of new antibodies and their selection is a time-dependent process, all diseases that take a very rapid course, such as viral infections with exponential viral replication in the body or bacterial infections that enter the blood and form sepsis, are particularly difficult for the body's immune system to fight. Often, the body's immune system ultimately does not have enough time to generate appropriate immune responses. With a GSSV, a way is provided to slow down very fast-moving viruses or bacterial infections so that the body's own immune system has enough time for an effective response to fight the pathogens.

However, even initially successful therapies that kill bacteria in the body, for example, may ultimately be unsuccessful because the toxins (endotoxins) released by the killed bacteria trigger negative effects in the patient's body that can lead to death. A GSSV provides a means to inhibit the negative effects of toxin release such that the body does not develop negative consequences such as septic complications or sepsis. That is, the GSSV effected according to the invention is a measure by which an effective antibiotic therapy, but one that may be associated with severe/fatal side effects, can be made tolerable in such a way that it can be used for the benefit of the patient.

Also endogenous but uncontrolled cells growing in the body, such as tumor cells, which grow invasively and form metastases, finally lead to an exponential growth of these aggressive tumor cells (cancer cells), which then in the majority of cases lead to a metabolic death of the cancer patient. In these cases, a GSSV is able to slow down the growth of metastatic cancer cells such that exponential growth is prevented, or existing exponential growth of these cells is inhibited such that they proliferate only slowly or not at all. The use of GSSV according to the invention represents a significant difference from previous therapeutic approaches in oncology, because it is not a therapy specifically directed at the undesired cells (cancer cells), but aims at and effects a non-specific inhibition of the metabolism of all the body's own cells. GSSV and its use in the field of oncology thus represent a primarily not curative but palliative approach, which above all provides the cancer patient with more time to live, and does so without limiting the quality of his or her life, since, in contrast to conventional cancer therapies, GSSV has no or only minor side effects.

In a preferred embodiment, the inhibitory structural analog or inhibitory functional analog is an inhibitory thiamine analog—hereinafter also referred to as thiamine antagonist—, in particular oxythiamine and/or benfo-oxythiamine and/or a benfo-oxythiamine analog and/or a benfo-oxythiamine derivative.

The terms "inhibitory thiamine analogues", in the singular "inhibitory thiamine analogue", and thiamine antagonist(s) stand here for a (each) substance that (i) preferably belongs to the small molecules (small compounds), i.e. to the organic compounds with a molecular weight below 900 Dalton, which influence a biological process, and that preferably in addition (ii) is either (a) a structural analogue of thiamine, in particular a thiamine derivative which inhibits the enzyme activity of thiamine-dependent enzymes, or (b) a functional analogue of thiamine, in particular an active ingredient which has no analogy to the thiamine structure but functionally inhibits the action of thiamine either by competing with thiamine for binding to the thiamine-dependent enzyme or by inhibiting the action of thiamine bound to the thiamine-dependent enzyme.

Thiamine-dependent enzymes catalyze an extremely wide range of catabolic, anabolic, and energy-releasing metabolic reactions, enabling the associated metabolic pathways.

With the thiamine antagonist(s) of the invention, this group of enzymes, namely all enzymes that use thiamine as a co-enzyme, is blocked in its activity and thus the biochemical processes of the cell are interfered with on a broad basis and at many sites simultaneously. In particular, a large number of essential catabolic, anabolic and energy-releasing metabolic pathways are specifically slowed down or inhibited or completely blocked. In particular, inhibited catabolic reactions include the breakdown of carbohydrates and proteins with energy release in the form of energy-rich bonds such as acetyl-CoA and ATP. Acetyl-CoA plays a crucial role in the formation of new cell structures, especially fatty acids, lipids and cholesterol. These components play an essential role in the formation of cell membranes and membranes of organelles such as mitochondria, which in turn play an important role in the release of energy from hydrogen and its fixation in the form of the energy-rich compound ATP.

The use of thiamine antagonists according to the invention, for example, causes, among other things, inhibition of all alpha-keto acid dehydrogenases, i.e. inhibition of a family of enzymes that is crucial for the degradation of carbohydrates and proteins and for the release of energy therefrom. In particular, this includes the three enzymes pyruvate dehydrogenase, α-ketoglutarate dehydrogenase, and branched-chain alpha-keto acid dehydrogenase, each of which decarboxylates and forms an energy-rich bond in the form of acetyl-CoA, and each of which splits off hydrogen to form NADH+H.$^+$ Inhibition of alpha-keto acid dehydrogenases by thiamine antagonists leads to inhibition of catabolic metabolic pathways and the resulting possible release of energy from carbohydrates and proteins. Both the reactions that directly form energy-rich bonds such as acetyl-CoA and the reactions that lead to the formation of ATP by oxidation of the released hydrogen are inhibited. Thiamine antagonists thus represent very good starting points for inhibiting the release of energy and the formation of energy-rich bonds such as acetyl-CoA and ATP.

Other important thiamine-dependent enzymes inhibited with the use of thiamine antagonists according to the invention are, for example, the transketolases, which do not carry out decarboxylation and hydrogen cleavage and allow the conversion of sugars such as the formation of riboses from glucose.

Since essential anabolic metabolic processes in the cell require the supply of energy, it is possible to use thiamine antagonists to inhibit, via the inhibition of catabolic and energy-releasing metabolic reactions, essential energy-dependent anabolic metabolic reactions that are necessary to generate building blocks for the maintenance, repair, and new formation of cell structures. For example, the synthesis of nuclear DNA during mitosis or the repair of DNA damage depend on the presence of both the four base building blocks and sufficient energy in the form of ATP for the energetic activation of the base building blocks. In principle, the same applies to the synthesis and repair of RNA.

The technical effect of the use of thiamine antagonists according to the invention for the purpose of effecting (bringing about) the GSSV according to the invention is thus primarily the fact that in the cells, through the inhibition of thiamine-dependent enzymes, both the catabolic metabolism (in particular of carbohydrates and proteins) and the anabolic metabolism and also the release of energy and its fixation in energy-rich compounds are massively inhibited. The inhibition of the metabolism thus involves an extremely large number of different adjusting screws in the form of different thiamine-dependent enzymes.

In a preferred embodiment of the use according to the invention, the inhibitory thiamine analog is the substance benfo-oxythiamine (hereinafter "B-OT" for short).

B-OT is a precursor ("pro-pharmacon", "prodrug") of oxythiamine B-OT can be administered orally and releases oxythiamine shortly after absorption into the mammalian organism. Oxythiamine inhibits thiamine-dependent enzymes. In mammals, the conversion (metabolization) of B-OT to oxythiamine occurs in the blood. Through the bloodstream, B-OT can reach all cells in all parts of the body.

In vivo pharmacokinetics data have shown that oxythiamine is present in significant amounts in the brain after B-OT is administered, implying that oxythiamine crosses the blood-brain barrier.

In vivo pharmacokinetics data from rat experiments on the bioavailability of B-OT after oral administration have shown that 0% B-OT is measurable in the blood, that means de facto the prodrug form is not measurable in the blood, but that 44% of the total amount of B-OT administered is measurable in the blood in the form of oxythiamine (OT). This means that there is a very efficient cleavage of B-OT into OT, and a high percentage amount of OT is present in the blood. Thus, B-OT is a pharmacokinetically good and orally applicable substance that allows good and efficient delivery of OT. Since OT usually must/should be administered intraperitoneally, the oral administration of B-OT represents an important advantage in comparison. The bioavailability and absorption of B-OT is also more suitable for human therapy due to the more lipophilic basic structure of B-OT compared to OT. Compared to OT, B-OT is thus better, easier and safer to use as a drug.

The chemical structure (structural formula) of benfo-oxythiamine can be given as follows:

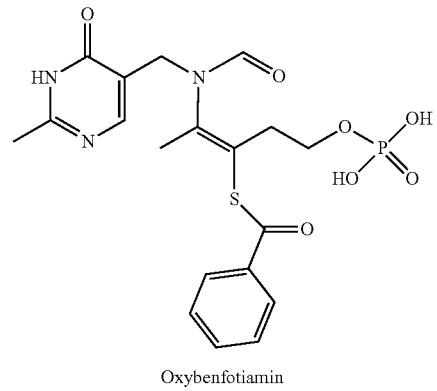 [SMILES: C/C(=C(/CCOP(=O)(O)O)SC(=O)c1ccccc1)N(C=O)Cc1cnc(C)[nH]c1=O]

Oxybenfotiamin

The production of Benfo-Oxythiamine (B-OT) according to the EU GMP Guide for Human and Veterinary Medicinal Products is well established in the state of the art, which allows the use of Benfo-Oxythiamine in mammals (e.g. dogs, cats) and especially in humans.

Drug development has so far been guided by the idea that agents must be found that kill or at least inhibit the attackers in the mammalian organism/human organism system with symbiont, commensal and parasite colonizations. To achieve this, selectively acting drugs must be found that inhibit the attacker but not the defender (e.g., humans) From this perspective, it makes no sense to find a drug that inhibits both the attacker and the defender. However, there are situations in which it does make sense to inhibit both the attacker and the defender at the same time. One of these situations is, for example, when the attacker (or attackers) multiplies (multiply) in the body of the defender to such an extent that sepsis develops.

Sepsis is a systemic response of the organism to an uncontrolled infection and is usually caused by bacteria, but increasingly also by fungi. Sepsis is a life-threatening condition that occurs when the body's response to an infection damages its own tissues and organs. Sepsis can lead to shock, multiple organ failure and ultimately death, especially if it is not recognized early and treated quickly. Sepsis is the leading cause of infection-related death worldwide.

Sepsis is one of the most common causes of death. Infections triggered by injuries or contamination during surgery can develop into explosive bacterial growth. Toxins are released that lead to multi-organ failure and ultimately to the death of the patient.

To date, the only chance of saving the patient is to kill the bacteria as quickly as possible with an effective antibiotic. But even then, the patient may die because the toxins (endotoxins) released by the killed bacteria can trigger septic complications or sepsis via signaling pathways (e.g. toll-like receptors or inflammatory signaling pathways). Currently, there is often not enough time to select the appropriate effective antibiotic via laboratory testing, and there is a risk of selecting a drug that is ineffective due to resistance. Moreover, even if the effective antibiotic is selected, there is a risk that the toxins released when the antibiotic kills the bacteria will lead to septic complications or sepsis.

With the GSSV effected according to the invention, not only are the patient's own cells and the signaling pathways via which toxins can trigger septic complications or sepsis affected, but bacterial metabolism is also addressed and can be inhibited. This means that the cell division ability of the bacteria is disrupted and their explosive multiplication is prevented. This saves time, which can be used to select the appropriate drug via laboratory tests and then use it in a targeted manner. In addition, GSSV also inhibits human metabolism and related reactions or excessive reactions of the body in response to infection. In addition to the damaging processes emanating from the toxins released from bacteria (e.g., endotoxins), overshooting reactions, e.g., overshooting immune reactions, are also inhibited. In many cases, it is the body's responses via signaling pathways or immunological reactions that can cause severe damage or even death to the patient. The dual action of GSSV in the form of simultaneous action on bacterial metabolism and patient metabolism is of particularly beneficial effect for therapy and patient survival in bacterial infections and the associated risk of sepsis development.

By effecting a stronger GSSV according to the invention, bacterial growth can be slowed down to such an extent that little or no damage is caused by the bacterium and the patient's own immune system has considerably more time to develop antibodies against the bacteria.

In other words, simultaneous (at the same time and parallel) blocking of the metabolism of the aggressor (e.g., *bacterium, fungi*) and the metabolism of the defender (human) can prevent the ratio of bacterial proliferation and/or fungal growth with accompanying damage to the body to the defense performance of the patient's organism from deteriorating, because an increase in bacterial proliferation and/or fungal growth relative to the body's defense performance is prevented. Simultaneous inhibition of attacker(s) and defender(s) does not cure per se, but it stabilizes the patient's situation and buys time to identify therapies that are effective. In addition, it opens the possibility of suppressing negative-acting responses of the body to bacteria and released toxins. In the case of an infestation with a *bacterium* that cannot be contained and eliminated by the human immune system, the use according to the invention makes it possible to prevent the uncontrolled proliferation of this *bacterium* in the body. The simultaneous inhibition of the metabolism of the bacteria and the patient's organism leads to a kind of shut down of both metabolisms, so that a stable situation is created, which provides time, for example, to test the bacteria with regard to resistance to antibiotics and thus to find out which antibiotic can be used with a good prospect of effectiveness. In addition, the negative consequences of successful elimination of the bacteria, such as the negative effects of the toxins released in the process, can also be inhibited by inhibiting signaling pathways activated by toxins or other factors released from bacteria.

It is therefore also an object of the present invention to provide an inhibitory structural analog or functional analog according to the invention, preferably an inhibitory thiamine analog (thiamine antagonist), in particular oxythiamine, and particularly preferably benfo-oxythiamine and/or a benfo-oxythiamine analog and/or a benfo-oxythiamine derivative, for use in the treatment of a patient with bacterial disease (infection). The use is preferably as monotherapy or as co-therapy with at least one further drug, in particular a drug with antibacterial activity. The use is aimed in particular at suppressing the effect of bacterial endotoxins on the patient's organism, in particular those endotoxins which are released as a result of the bactericidal action of the further medicament.

In accordance with the invention, the inhibitory active ingredient according to the invention is preferably administered orally and in accordance with a dosage regimen comprising, for example, the following:

The recommended dosage is (based on 60 kg body weight):
on the first day twice about 40 mg;
on the second day twice about 20 mg;
on the third day twice about 10 mg.

It is also an object of the present invention to provide an inhibitory structural analogue and/or inhibitory functional analogue according to the invention, preferably an inhibitory thiamine analogue (thiamine antagonist), in particular oxythiamine, and particularly preferably benfo-oxythiamine and/or a benfo-oxythiamine analogue and/or a benfo-oxythiamine derivative, for use in the treatment of a patient with a disease originating from/caused by fungi, preferably as monotherapy or as co-therapy with at least one further drug.

In accordance with the invention, the inhibitory active ingredient according to the invention is preferably administered orally and in accordance with a dosage regimen comprising, for example, the following:

The recommended dosage is (based on 60 kg body weight):
the first day twice about 30 mg;
on the second day twice about 15 mg;
on the third day twice about 5 mg.

It is also an object of the present invention to provide an inhibitory structural analogue and/or inhibitory functional analogue according to the invention, preferably an inhibitory thiamine analogue (thiamine antagonist), in particular oxythiamine, and particularly preferably benfo-oxythiamine and/or a benfo-oxythiamine analogue and/or a benfo-oxythiamine derivative, for use in the treatment of a patient with sepsis or impending sepsis. The administration of this inhibitory agent according to the invention is here preferably carried out orally and according to a dosage regimen comprising, for example, the following:

a) The recommended dosage in case of already pre-existing sepsis is (at 60 kg body weight):
  on the first day twice about 40 mg;
  on the further day twice about 20 mg;
  on the third day twice about 10 mg.
(b) The recommended dosage for prophylaxis of sepsis is (at 60 kg body weight):
  on the first day twice about 20 mg;
  on the second day twice about 10 mg;
  on the third day twice about 5 mg.

It is further an object of the present invention to provide an inhibitory structural analogue and/or inhibitory functional analogue according to the invention, preferably an inhibitory thiamine analogue (thiamine antagonist), in particular oxythiamine, and more preferably benfo-oxythiamine and/or a benfo-oxythiamine analogue and/or a benfo-oxythiamine derivative, for use in the treatment of a patient with viral disease (or infection). The administration of this inhibitory agent according to the invention is here preferably carried out orally and according to a dosage regimen comprising, for example, the following:

The recommended dosage is (based on 60 kg body weight):
(a) In case of already strong viral infection or strong (exuberant) immunological reaction of the body:
  on the first day twice about 40 mg;
  on the second day twice about 20 mg;
  on the third day twice about 10 mg.
(b) In case of moderate symptoms for prophylaxis of severe viral infestation:
  on the first day twice about 20 mg;
  on the second day twice about 10 mg;
  on the third day twice about 10 mg;
  from the fourth to the seventh day, about 5 mg once a day.
(c) If symptoms are mild to absent, for prophylaxis of viral reinforcement:
  In the first week twice a day about 4 mg;
  in the second week twice a day about 3 mg;
  in the third week, about 3 mg once a day.

Acute viral diseases such as influenza can be fatal in patients, especially in those with a compromised immune system. What is also special about viral diseases is the explosive growth with which the viruses can replicate and subsequently attack more and more body cells. Recent studies show that drugs that limit the viruses' ability to replicate can usually only achieve therapeutic success if they are used at an early stage. If the viral load is too high, they are usually ineffective.

With the GSSV effected according to the invention, all cells in the patient's body are affected. When viruses attack the body's own cells, the cell's metabolism is activated to provide the building blocks for virus replication. Metabolic blockade counteracts this and inhibits the viruses' ability to replicate. This reduces the viral load and the anti-viral effect of drugs can be used to effectively combat the viruses.

By effecting a stronger GSSV in the patient organism according to the invention, the multiplication of the viruses can be slowed down so that hardly any or no more damage is caused by the viruses and the human immune system has considerably more time to develop antibodies against the viruses.

In other words, the GSSV according to the invention can also be used in patients with viral diseases, even though viruses do not have their own metabolism. Since viruses reprogram the host cell in such a way that the metabolism of the host cell makes it possible for the viruses to multiply, an inhibition of the metabolism of the virus-infected defender is a new method of treating viral diseases that has not been used before. Viruses that are new to humans and very dangerous to them, such as the coronavirus SARS-COV-2 and the associated disease COVID-19, lead to immunological and cellular reactions that can be fatal. Often, excessive reactions, such as excessive cytokine formation, are the main reason for the severity of the viral disease or the death of the patient. By inhibiting the metabolism of the patient's cells infected by the virus, it is possible to slow down any reaction and thus also excessive reactions of the patient's body to a viral infection. By slowing down the metabolism, all reactions associated with the viral infection are slowed down. This not only achieves that the viral load is lowered at the peak, but also that all reactions triggered by the viral infection, including the body's reaction to the viral infection, can be specifically slowed down in this way. The slowing down of the metabolism can be achieved in a stepless manner by increasing the concentration of the active ingredient, which means that the slowing down of the metabolism can be adjusted very well to the necessary slowing down. This allows the entire infection process and the human body's response to it to be slowed down in a controlled and stepless manner Excessive, too strong responses of the immune system can thus be prevented, so that the damage caused by the excessive immune system can be avoided. The inhibition of the metabolism in the human organism (and mammalian organism), and the concomitant inhibition of the multiplication of the virus in the patient organism can be quantitatively carried out in such a way that the virus multiplication continues to take place, but the process is so slow that no or no severe damage is triggered by the viruses, or by overshooting of the immune system. By stretching out the viral infection over time and slowing down viral replication in the body (i.e., the patient's organism), it is possible to give the patient's immunological response more time to develop an immune response. Ultimately, many patients die because some immune responses, such as exuberant immune responses, are too strong, but on the other hand, the immune response per unit time is too with regard to the formation of antibodies. Even if the infected person's immune system can produce neutralizing antibodies, these must be available quickly enough to keep the virus in check or eliminate it. Therefore, the immune system must be able to mount a successful immune response within a few days to produce antibodies to protect the patient from a severe course or death. By slowing down the infection process in the (patient's) body by means of the metabolic slowdown GSSV according to the invention, the immune system is given considerably more time to enable a successful immune response with regard to the formation of antibodies.

A further object of the present invention is an inhibitory structural analogue and/or inhibitory functional analogue according to the invention, preferably an inhibitory thiamine analogue (thiamine antagonist), in particular oxythiamine, and particularly preferably benfo-oxythiamine and/or a benfo-oxythiamine analogue and/or a benfo-oxythiamine derivative, for use in the treatment of a patient with an immunological disease, in particular an inflammatory disease and/or an autoimmune disease. Autoimmune diseases in this context include in particular systemic lupus erythematosus (SLE) and those forms of disease which occur with an intermittent course (in relapses), in particular rheumatoid arthritis and/or multiple sclerosis and/or inflammatory bowel diseases such as ulcerative colitis, Crohn's disease and/or inflammatory/degenerative diseases, in particular of the skeletal system such as Morbus Bechterew.

In accordance with the invention, the administration of this inhibitory active ingredient according to the invention is preferably carried out orally and in accordance with a dosage regimen comprising, for example, the following:

The recommended dosage is (based on 60 kg body weight):
(a) When attacks (relapses) occur:
    about 15 mg once a day for a week.
(b) For prophylaxis of attacks (relapses):
    about 3 mg once a day for a month.

Autoimmune processes are often characterized by excessive or incorrect immune reactions. Many autoimmune diseases occur in relapses. In the phase of an attack (relapse), the immune system is particularly active and causes inflammatory events, as a result of which healthy cells can be excessively damaged. In most cases, the general condition of the patient worsens after the attack (relapse) compared to the condition before.

When the immune system is activated, new cell formation is stimulated, cells differentiate to perform specific tasks, and cell activation increases metabolic activity. The GSSV effected according to the invention also affects (influences) the immune cells, whose activation and multiplication is limited under the GSSV.

Chronic autoimmune diseases such as rheumatism, Crohn's disease, ulcerative colitis and others are characterized by increased inflammation. Since these are chronic processes, it is possible to control the diseases permanently by slowing down the metabolism by means of the use and effect of the GSSV according to the invention. For this purpose, lower doses are selected so that healthy cells are not permanently damaged, but the inflammatory process is reduced overall by the slowdown.

The drug metabolism slowdown according to the invention allows the improvement of disease courses that are characterized by disease attacks (relapses9. One example of a disease that progresses intermittently is multiple sclerosis. In 90% of cases, patients suffer from relapsing multiple sclerosis. Slowing down the metabolism makes it possible to treat such relapsing diseases by slowing down the metabolism when relapses occur and thus counteracting the development of the relapse.

This application according to the invention can also be used to reduce the risk of organ rejection after transplantation.

It is further an object of the present invention to provide an inhibitory structural analogue and/or inhibitory functional analogue according to the invention, preferably an inhibitory thiamine analogue (thiamine antagonist), in particular oxythiamine, and particularly preferably benfo-oxythiamine and/or a benfo-oxythiamine analogue, for use in the tumor treatment of a patient, in particular in the treatment of cancer (malignancies) of a patient (human or mammalian) as monotherapy or as pre- or co-therapy of chemotherapy and/or radiotherapy and/or targeted cancer therapy.

The primary purpose of this use in cancer patients is a multiple simultaneous inhibition of the enzymes of the enzyme group and thus throttling/slowing down of the anabolic, catabolic and energy-providing metabolic processes in all cells of the body, i.e. in all healthy cells and also in the uncontrolled growing cells (tumor cells). Therefore, the use of GSSV does not specifically target tumor cells, but in principle slows down the metabolism of all body cells. As a consequence, healthy cells and also uncontrolled growing cells like tumor cells are less able to perform catabolic, anabolic and energy releasing metabolic processes. As a result, the formation of radicals in the cell is increased by both endogenous processes and exogenous actions such as irradiation, and the neutralization of radicals is slowed, thus increasing radical stress and also DNA damage. Cancer cells are much less able to respond to stress (e.g., radical stress) or damage (e.g., as a result of chemotherapy and/or radiation therapy), and the threshold at which stress and damage lead to their death (apoptosis) is lowered. In other words: If established tumor or cancer therapy is started in a phase before or after metabolic blockade, the cell's ability to repair itself is limited. Cell repair requires substrates that are converted to end products by enzymes. Energy is used for this purpose. If the cell lacks sufficient substrates and energy as a result of the GSSV caused according to the invention, enzymatic reactions that are required for various areas of cell repair cannot occur. As a result, cells that could normally repair existing damage are led to cell death. At the same time, RedOx homeostasis is also affected so that the ratio of oxidizing to reducing processes is raised in favor of oxidizing processes. Both effects, the reduction of substrates and available energy in the cell as well as the shift of RedOx homeostasis in favor of oxidative processes lowers the threshold for cell death including tumor cells. Thus, the GSSV therapy leads to the weakening of cancer cells and consequently to the lowering of the threshold value of cells for their death. Due to this lowering of the threshold value for cell death, the cancer cell is less able to withstand the damaging effect of an subsequent or concurrent chemotherapy and/or radiotherapy with established agents and/or targeted cancer therapies and also not evade them (because alternative metabolic processes that could serve as "evasion and bypass pathways" for the one damaged by the therapeutic agent are also inhibited or almost completely blocked).

Many tumor therapies aim to directly damage tumor cells and thus trigger cell death. A tumor comprises several million or more tumor cells. The degree of damage to a cell is dose-dependent. It cannot be guaranteed that the dose is the same for all tumor cells. At lower doses, the damage is not sufficient to kill the cell or the cell can activate its repair mechanisms to repair damage and thus prevent cell death. Therefore, it is hardly possible to kill all cells at the same time with a cancer therapy.

Nevertheless, in order to achieve the greatest possible success, the state of the art uses active ingredients in high concentrations and accepts that patients have to deal with severe side effects.

The use of the co-enzyme antagonist according to the invention and the GSSV brought about thereby represent a useful supplement to practically all known therapeutic principles.

Especially in the context of co-therapy with established anti-tumour therapies, several catabolic, anabolic and energy-releasing/fixing metabolic processes can be inhibited or completely blocked simultaneously and, as required, gradually or as immediately as possible and moderately or more or strongly, specifically adapted to the type of co-therapy (anti-tumour therapy), by choosing the timing of the onset of GS SV in relation to the co-therapy (anti-tumour therapy). Since GSSV on the one hand causes a lowering of the threshold for tumor cell death and on the other hand counteracts malignant properties of tumor cells in such a way that they are less malignant e.g. form less lactic acid and thus grow less invasively, form less metastases, suppress the immune system less e.g. by inhibiting the acidic arrest of killer cells, whereby killer cells can attack and kill tumor cells again or better, it creates the conditions for any subsequently applied established anti-tumor therapy, in particular established cancer chemotherapy and/or radiation therapy and/or targeted cancer therapy, to be more efficiently effective, because the cell damage thus produced triggers the death of the tumour cells (and especially cancer cells) concerned more quickly, more reliably (i.e. with greater probability) and in greater quantity/number.

In particular, because of this dual effect, the GSSV effected according to the invention can also be used as monotherapy.

The dosage regimen for the inhibitory co-enzyme analogue according to the invention in tumor treatment depends on whether it is a monotherapy or a pre- or co-therapy. If the use according to the invention takes place as a pre- or co-therapy in combination with established cancer therapies, the dosage regimen for the inhibitory co-enzyme analogue according to the invention varies depending on the additionally applied cancer chemotherapy and/or radiotherapy and/or targeted cancer therapy.

In the case of combining radiotherapy with the use of the inhibitory co-enzyme analogue according to the invention, for example and preferably in the form of the thiamine antagonist B-OT, B-OT is administered after the radiotherapy. This avoids B-OT leading to inhibition of cell proliferation and DNA duplication and reducing the effect of radiotherapy because non-proliferating cells are less sensitive to radiation. Instead, it is achieved that at the time of irradiation, cell proliferation of tumor cells is in full swing, radiotherapy induces maximal damage, and subsequent administration of B-OT inhibits repair of radiation damage, thereby promoting tumor cell death.

In the case of the combination of chemotherapy using classical cytostatics (i.e. cell type non-specific cell proliferation inhibitors) with the use of the inhibitory co-enzyme analogue according to the invention, for example and preferably in the form of the thiamine antagonist B-OT, B-OT is administered prior to the start of chemotherapy so that at the time of the start of chemotherapy some of the thiamine-dependent enzymes are already inhibited.

In the case of combining a targeted cancer therapy (e.g., using agents such as sorafenib or imatinib) with the use of the inhibitory co-enzyme analog according to the invention, for example and preferably in the form of the thiamine antagonist B-OT, the administration of B-OT should preferably be started about two days before the start of the targeted cancer therapy in order to optimally promote the effect of the targeted therapies.

In the case of combining surgical tumor removal with the use of the inhibitory co-enzyme analogue according to the invention, for example and preferably in the form of the thiamine antagonist B-OT, the B-OT administration is carried out as a kind of pre-treatment before the surgical intervention. It preferably starts about three days before surgery so that by the time of surgery the number of disseminating tumor cells (i.e., tumor cells released into the blood or other body fluids) is reduced and their invasiveness and metastatic potential is inhibited. This reduces the likelihood of the formation of locally growing recurrences and of distant metastases.

According to the invention, the inhibitory agent according to the invention is preferably administered orally in the course of a co-therapy and preferably according to a dosage regimen comprising the following:
(a) When used in combination with radiotherapy:
on the day of radiotherapy before radiotherapy once about 1-150 mg, preferably about 10-75 mg, especially preferably about 30-50 mg;
on the day after radiotherapy once about 1-70 mg, preferably about 3-40 mg, particularly preferably about 4-20 mg;
on the second day after radiotherapy once about 1-40 mg, preferably about 3-25 mg, particularly preferably about 4-18 mg.
(b) When used in combination with chemotherapy, especially with the use of cytotoxic drugs:
the day before chemotherapy once about 1-150 mg, preferably about 10-75 mg, especially preferably about 30-50 mg;
on the day of chemotherapy once about 1-150 mg, preferably about 10-75 mg, especially preferably about 5-50 mg;
on the day after chemotherapy once about 1-100 mg, preferably about 10-75 mg, especially preferably about 5-50 mg.
(c) When used in combination with one, or more, targeted cancer therapy(s), in particular using imatinib and/or sorafenib and/or erbitux and/or avastin and/or gemcitabine:
the day before chemotherapy once about 1-100 mg, preferably about 10-75 mg, especially preferably about 5-50 mg;
on the day of chemotherapy once about 1-100 mg, preferably about 10-75 mg, especially preferably about 5-50 mg;
on the day after chemotherapy once about 1-100 mg, preferably about 10-75 mg, especially preferably about 5-50 mg.
(d) When used as monotherapy or in combination with one or more other therapy(ies), where the use lasts longer than one week, especially longer than two weeks or longer than three weeks or longer than four weeks:
per day about 1-30 mg, preferably about 2-15 mg, very preferably about 3-10 mg, and in each case as a single dose or in the form of several partial doses.
For example, a dose of 30 mg or 15 mg per day may be administered as a single dose of 30 mg or 15 mg, respectively, or in appropriately smaller doses of, for example, 2×15 mg or 1×5 mg and 1×10 mg per day.

A dosage regimen that has worked well in practice is:
(a) Recommended dosage when used in combination with radiotherapy:
On the day of radiotherapy before radiotherapy once about 34 mg;
the day after radiotherapy once 12 mg;
on the second day after radiotherapy 5 mg.
(b) Recommended dosage when used in combination with chemotherapy using classical cytostatic agents:
once 25 mg the day before chemotherapy;
on the day of chemotherapy once 13 mg;
the day after chemotherapy 6 mg.
(c) Recommended dosage when used in combination with targeted cancer therapy (e.g., using sorafenib or imatinib):
two days before therapy once 10 mg;
once 8 mg the day before therapy;
once 6 mg on the day of therapy;
the day after therapy 4 mg.

The dose quantities given above and also all dose quantities given below apply to a human with a body weight of 60 kg and must be adjusted accordingly to the patient's actual body weight in individual cases.

The dose levels apply especially if the applied agent is the thiamine antagonist B-OT.

In the mechanism of action of established tumor therapies, a basic distinction can be made between direct therapies, which aim to damage the tumor cell, and indirect therapies, which trigger activation of the immune system to subsequently damage/destroy tumor cells. In addition to these two established therapeutic strategies, GSSV offers a new avenue of therapy that, although not curative, can significantly prolong the survival of cancer patients by inhibiting tumor spread, including its invasive growth behavior and the formation of new metastases. Since it is precisely the spread and metastasis of tumors that are the most common and in many cases the decisive reason for the death of patients, it is a milestone clinically and for the survival of cancer patients that with the co-enzyme antagonist according to the invention, particularly in the form of B-OT, an active substance is available that can inhibit invasiveness and metastasis.

The use of the active ingredient (drug) according to the invention (i.e. the co-enzyme antagonist according to the invention, in particular in the form of B-OT) for the purpose of inhibiting invasiveness and metastasis in a patient is preferably not in combination with chemo- and/or radiotherapies, but as monotherapy.

In the case of advanced tumor disease, the inhibitory co-enzyme analogue according to the invention is used, for example and preferably in the form of the thiamine antagonist B-OT, preferably as monotherapy.

According to the invention, the administration of the active ingredient according to the invention in the course of monotherapy is preferably carried out orally and according to a dosage regimen comprising, for example, the following:
(a) Recommended dosage—variant A:
5 mg daily for one week, followed by no administration for one week, then again 5 mg daily for one week, followed by no administration for one week.
(b) Recommended dosage—variant B
2.5 mg daily for one month.

The present invention thus offers several further options for cancer therapy. On the one hand, therapy can be carried out with lower doses without thereby jeopardizing the success of the therapy. This new option is particularly advantageous for therapies with severe side effects, which often have to be discontinued because the side effects are too severe. On the other hand, malignant characteristics such as invasiveness and metastasis can be inhibited, which does not cure the patient, but stabilizes the patient's situation (stable disease). Furthermore, the effect of the immune system especially that of killer cells killing tumor cells can also be increased by inhibiting the lactic acid production of tumor cells, thereby counteracting the acid-induced blockade/defense of the attack of killer cells by tumor cells. The co-enzyme antagonist according to the invention, for example and in particular B-OT, decreases the lactic acid production of tumor cells and thereby decreases the acidic arrest of the killer cells, whereby the tumor cells can then be better attacked and killed by killer cells.

In particular, the beneficial increase in efficiency of established tumor therapies also comprises (a) requiring less drug to achieve the same effect (because the threshold for die-off has been lowered, a lower dose of the drug therapeutic and/or radiation therapy is required to kill the cells), and (b) additional cells die off (because: Tumors generally comprise a heterogeneous mixture of different tumor cells, and lowering the threshold of death by using co-enzyme antagonists of the invention means that cancer cells that would not have died under conventional therapy now do die.)

The effect of cancer therapies on tumor cells always depends on the dose. A tumor comprises millions of cells and no therapy can guarantee that the dose of the active agent/radiation is the same in all cells. There will often be a proportion of cells where the drug will cause damage without causing cell death. Each cell has repair mechanisms to repair damage caused. The repair takes place via enzymatic reactions, which require substrate and energy for this purpose. If these are not present in the cell, or only to a limited extent, because the cell metabolism was previously slowed down or inhibited, the ability to repair is limited. As a result, cells with less extensive damage from chemotherapy and/or radiotherapy and/or targeted cancer therapy then also suffer cell death.

The use according to the invention does not distinguish between healthy and degenerated cells. Via its dosage regime (in particular timing of the start of the GSSV in relation to the start of additionally applied established cancer therapies, time intervals and amounts of the administered co-enzyme antagonist) as pre- or co-therapy or as monotherapy, the strength and duration of the effected GSSV can be varied and precisely controlled. In other words, the provision of essential substrates required for downstream specific enzyme reactions is blocked in the tumor cells (and also in all other body cells) for a predetermined limited period of time. This period of time (of the co-therapy or mono-therapy) is selected or dimensioned in such a way that the extent of the damage triggered in the cells is selected in such a way that after termination of the blockade (by discontinuation of the drug according to the invention) above all the healthy body cells can restart their metabolism, restart all enzymatic processes and do not suffer (carry away) any permanent damage.

Cancer patients often exhibit an almost explosive growth of cancer cells, especially when tumors no longer grow locally but invasively and metastasize. Cancer patients with very rapidly progressing disease, such as metastatic forms of cancer, often have only a few months or even weeks to live. Currently, these cancer patients only have the choice of therapies, such as chemotherapy, which have massive side effects, massively reduce the quality of life and thereby only allow a small extension of life. In this case, a cancer patient virtually buys an extension of life by e.g. one month and pays for it by suffering from pain and nausea during this month, feeling bad overall and being so weakened that he cannot lead a good life. With the GSSV effected according to the invention, it is now possible to slow down the metabolism of the cancer patient and the cancer growing in him in such a way that the patient's lifetime can be prolonged without causing pain or such a weakening of the patient that significantly reduces his quality of life. With a GSSV that produces a 50% slowing of the patient's metabolism in both his healthy cells and his cancer cells, it is possible to increase the patient's lifespan by 100% without any associated side effects such as pain or nausea.

GSSV therapy according to the invention can also be used in the case of glioblastomas and other cancer tumors (malignancies) in the brain with good prospects of success, in particular also as co-therapy with established chemotherapy and/or radiotherapy and/or targeted cancer therapy.

It is also an object of the present invention to provide an inhibitory structural analogue and/or inhibitory functional analogue according to the invention, preferably an inhibitory thiamine analogue (thiamine antagonist), in particular oxythiamine, and more preferably benfo-oxythiamine and/or a benfo-oxythiamine analogue, for use in the treatment of a patient as a pretreatment prior to surgical interventions and/or drug therapies. In accordance with the invention, the administration of this inhibitory agent according to the invention is here preferably carried out orally and according to a dosage regimen comprising, for example, the following:

The recommended dosage is:
two days before surgery once daily 4 mg (morning, or noon, or evening);
on the day of surgery before surgery 5 mg.

Preventive use of the application according to the invention and GSSV effected therewith before surgical interventions offers the advantage that adverse side effects as a result of the intervention and any complications are slowed down. Such complications can be excessive reactions of the body, e.g. excessive immune reactions or triggering of programmed cell death. GSSV effected according to the invention can also be used prior to drug therapies in order to reduce or avoid side effects, precisely because the metabolism is slowed down.

It is further an object of the present invention to provide an inhibitory structural analogue and/or inhibitory functional analogue according to the invention, preferably an inhibitory thiamine analogue (thiamine antagonist), in particular oxythiamine, and particularly preferably benfo-oxythiamine and/or a benfo-oxythiamine analogue, for use in the treatment of a patient with craniocerebral trauma. In accordance with the invention, the administration of this inhibitory agent according to the invention is here preferably carried out orally and in accordance with a dosage regimen comprising, for example, the following:

Recommended dose on the day the traumatic brain injury occurred about 45 mg;
recommended dose the following day about 5 mg;
recommended dose the day after about 3 mg.

In the case of particularly severe head injuries, the brain may swell as a result of the stress/injury to the brain, so that the internal pressure in the skull becomes too high, leading to consequential damage. Until now, in such cases, the skull has been opened surgically to provide more space for the brain. The use of GSSV therapy according to the invention makes it possible to specifically suppress the physiological reactions of the brain tissue to the accident-related impacts, so that the brain does not swell and there is no excessive intracranial pressure. By preventing excessive intracranial pressure, consequential damage caused by this is prevented.

Recommended dose on the day the severe head injury occurred 52 mg;
recommended dose on the following day 7 mg;
recommended dose on the five following days 3 mg.

It is further an object of the present invention to provide an inhibitory structural analogue and/or inhibitory functional analogue according to the invention, preferably an inhibitory thiamine analogue (thiamine antagonist), in particular oxythiamine, and more preferably benfo-oxythiamine and/or a benfo-oxythiamine analogue, for use in the treatment of a patient with nerve transection(s), in particular with spinal cord injuries and the risk of paraplegia or tetraplegia, or with a recent onset of paraplegia. In accordance with the invention, the inhibitory agent according to the invention is here preferably administered orally and according to a dosage regimen comprising, for example, the following:

Recommended dose on the day the spinal cord injury occurred 38 mg,
recommended dose on the following day 7 mg,
recommended dose on the five following days 3 mg.

Injuries resulting in partial or complete severing or crushing of the spinal cord usually also result in injury to blood vessels and the escape of blood. The contact of the blood with the injured nerves can lead to further damage to the nerves, and this damage is triggered or intensified by the blood pigment hemoglobin, among other substances. The blood pigment hemoglobin contains iron bound to it, which plays a role in oxidation processes and can trigger radicals or other cell damage. The aim of the GSSV effected according to the invention is, among other things, to counteract the damaging effects of the blood released by the blood vessel injuries or to reduce the damaging effects by inhibiting the effect of radical formation and/or the effect of the change in RedOx homeostasis with regard to triggering cell death, because the GSSV prevents or reduces the execution of cell death.

It is further an object of the present invention to provide an inhibitory structural analogue and/or inhibitory functional analogue according to the invention, preferably an inhibitory thiamine analogue (thiamine antagonist), in particular oxythiamine, and more preferably benfo-oxythiamine and/or a benfo-oxythiamine analogue, for use in the treatment of a patient with myocardial or cerebral infarction. In accordance with the invention, the administration of this inhibitory agent according to the invention is here preferably carried out orally and according to a dosage regimen comprising, for example, the following:

The recommended dosage is:
On the day the infarction occurred 35 mg,
the following day 5 mg,
the day after 3 mg.

Programmed cell death (apoptosis) is a process stored in the DNA and thus in the (human) organism to eliminate unwanted cells. This makes it possible to eliminate immune cells that are no longer desired in a planned manner, for example. Another example is apoptosis, which leads to the elimination of tumor cells. Apoptosis is thus a program that helps and protects the human organism. However, apoptosis can also have negative effects if it is triggered, for example, by a lack of oxygen or an infarction. For example, a lack of oxygen (ischemia) leads to a triggering of apoptosis and thus to a loss of important cells. A heart attack triggered by thrombosis of a blood vessel can then lead to an undersupply of oxygen and resulting apoptosis in cardiac cells. Even if a rapid supply of oxygen to the heart muscle is restored by intensive medical treatment, the apoptosis once triggered can lead to further consequential damage. The use according to the invention and GSSV effected thereby makes it possible to inhibit apoptosis in order to counteract the death of cells. GSSV inhibits metabolism and thereby also the apoptosis—initiating and apoptosis-executing processes and also reduces the oxygen consumption of the body's cells, so that damage caused by a lack of oxygen is reduced or prevented. GSSV thus acts at three levels: With the inhibition of metabolism, oxygen consumption and thus oxygen demand is lowered, so that apoptosis induced by ischemia is counteracted. With the inhibition of metabolism, the extent of apoptosis (initiation and execution of apoptosis) and its consequences are also reduced, as all metabolic processes are slowed down. With the slowing down of the damaging processes, time is also gained to apply drugs and therapies to counteract the damage.

The use according to the invention and thus effected GSSV thus also represents a therapeutic option in emergency medicine, namely a measure that can be carried out immediately at the scene of the accident. In patients with severe injuries, GSSV can already be induced at the scene of the accident, e.g. with oral administration of B-OT, whereby all damaging processes in the body can be slowed down or stopped completely. After arrival at the hospital, specific therapy can then be started earlier, relatively speaking, because damaging processes such as the triggering of apoptosis, which can take place during the time between the accident and the start of therapy in the hospital, have been significantly reduced as a result of the induced GSSV.

It is further an object of the present invention to provide an inhibitory structural analogue and/or inhibitory functional analogue according to the invention, preferably an inhibitory thiamine analogue (thiamine antagonist), in particular oxythiamine, and particularly preferably benfooxythiamine and/or a benfo-oxythiamine analogue, for use in the treatment of painful blunt injuries (traumas/trauma) of a patient, in particular strains, sprains or contusions. The administration of the inhibitory active ingredient according to the invention is here preferably carried out orally and according to a dosage regimen comprising, for example, the following indications:

The recommended dosage is:
on the day when the strain, sprain, contusion occurred 15 mg;
the following day 5 mg;
the day after 3 mg.

Less dramatic injuries to a patient such as painful blunt trauma, in particular strains, sprains or contusions, can also be better treated with the use according to the invention and GSSV brought about thereby. Until now, in these cases, attempts have been made to slow down the body's reactions to the injury with cooling measures. Often, cooling compresses or ice are used to cool down the injured body part. The principle of this therapy is based on the fact that enzymatic reactions are temperature-dependent. This dependence between the speed of the enzyme reaction and temperature is described mathematically by the so-called reaction speed-temperature rule (also van't Hoff s rule). An increase in temperature by 10 degrees Celsius leads to a doubling to tripling of the enzyme reaction speed. Conversely, lowering the temperature by 10 degrees Celsius leads to a halving to a third of the enzyme speed. Consequently, cooling the injured area results in a significant inhibition of the enzymatic reactions set in motion by the body as a consequence of the injury. However, the lowering of the tissue temperature is only possible to a certain extent, because excessive cooling leads to tissue damage. The GSSV according to the invention, on the other hand, allows the metabolism to be lowered even more than is possible with cooling, without causing irreversible cell and tissue damage. Moreover, cooling of the tissue with externally applied refrigerants such as ice is only gradual, being strongest near the refrigerant and much less pronounced further inside the tissue. Particularly in the case of deeper injuries such as joint injuries, cooling is only able to cool deeper tissue areas to a very limited extent.

In general, inhibition of metabolism caused by cooling is only applicable to a very limited extent, since the available temperature range extends at most to the freezing point. For a reduction from 37° C. to 1° C. (i.e., by 36° C.), assuming a factor of 3 for a 10° C. reduction, a maximum slowdown by a factor of about 50 would result. In the case of GSSV, this factor is unlimited, since inhibition of the metabolism by medication allows this to be carried out independently of temperature up to complete inhibition.

According to the invention, the choice of a suitable dosage regimen for the administration of the inhibitory agent of the invention, namely the co-enzyme antagonist, can be made for any desired use, in particular for use in a pre- or co-therapy in the treatment of cancer and/or for use in a continuous therapy lasting weeks or months, according to the following procedure, i.e. determined by a method comprising the following steps:

(1) on day 1:

(1a) selecting the co-enzyme antagonist/active ingredient (for example and preferably benfooxythiamine B-OT) and measuring the enzyme activity of a representative enzyme E from the enzyme group in question, i.e. from the group of enzymes dependent on the co-enzyme (for example and preferably the enzyme activity of transketolase in erythrocytes from the group of thiamine-dependent enzymes) in a first available (ready) body fluid sample I (for example and preferably a blood sample I) of the patient previously obtained.

(1b) Subsequently (i.e., on the same day) administering to the patient the co-enzyme antagonist/active ingredient (for example and preferably B-OT) in an amount/dose T1 which is suitable of inducing in the co-enzyme-dependent (for example and preferably thiamine-dependent) enzymes an inhibition of their original enzymatic activity, wherein a target value for the enzyme activity inhibition (inhibited enzyme activity) lasting (if necessary for weeks or months) is predetermined (defined) and aimed at;

(2) on day 2:

(2a) Measurement of the enzyme activity of enzyme E in a ready body fluid sample II (for example, and preferably blood sample II) of the patient obtained on that day;

(2b) Comparison of the enzyme activities measured in body fluid sample I and body fluid sample II (for example and preferably blood sample I and blood sample II) and calculation of the extent (scope, degree) of the reduction (inhibition) of the enzyme activity caused;

(2c) Subsequent (i.e., occurring on the same day) administration of the co-enzyme antagonist/active agent (for example and preferably B-OT) to the patient in an amount T2 (dose T2) determined (calculated) on the basis of amount T1 (dose T1) and the desired target value for enzyme activity inhibition and on the basis of the reduction in enzyme activity (as a result of administration of dose T1) calculated in step (2b). The amount T2 (dose T2) may be larger or smaller compared to the amount T1 (dose T1), i.e., there is an adjustment of dose T1 to dose T2 comprising a reduction or increase in the amount of co-enzyme antagonist/active ingredient (e.g., B-OT) administered on day 1.

(3) on day 3 and subsequent days until attainment of the targeted value for enzyme activity inhibition (i.e., until the target enzyme activity inhibition level is reached):

Repeating steps (2a) and (2b) and repeating step (2c) with the modification that the administration of the co-enzyme antagonist/active ingredient (for example and preferably B-OT) to the patient is carried out in an amount/dose T(i) which is determined (calculated) on the basis of the amount/dose of the previous day T(i-1) and the desired target value for enzyme activity inhibition and on the basis of the reduction in enzyme activity calculated in step (2b). The amount/dose T(i) may be larger or smaller compared to the previously administered amount/dose T(i-1), i.e., there is an adjustment of the dose T(i-1) to the dose T(i) comprising a reduction or increase in the previously administered amount of B-OT.

Optionally and preferably, in a step (4), the monitoring of medical parameters of the disease, for example the inhibition of the formation of new metastases or the growth of bacteria or fungi in the body, and of medical parameters of the basic functions of the patient's body, for example and preferably the number of heart beats per minute (pulse beat) and/or occurring loss of appetite and/or a loss of weight in the patient is carried out. Adjustment of the target value for the enzyme activity inhibition is performed in such a way that, on the one hand, the medical parameters of the disease reach the desired values and that, on the other hand, sufficient residual enzyme activity is still present, so that the basic functions of the patient's body are maintained in the long term.

In individual cases, it may prove necessary to correct the originally targeted inhibition value. On the basis of medical parameters of the particular disease to be treated, such as inhibition of the formation of new metastases or the growth of bacteria or fungi in the body, the target value of inhibition of enzyme activity should be set so that, on the one hand, the desired values for these medical parameters are achieved, but, on the other hand, sufficient residual enzyme activity is still present to enable the basic functions of the patient's body to be maintained in the long term. For example, the number of heart beats per minute (pulse rate) can be used to measure the basic function of the body. If the pulse rate becomes too high, the amount to be administered or dose of the co-enzyme antagonist/active ingredient (for example, the B-OT amount) must be reduced. Loss of appetite or weight loss in the patient can also be interpreted and used as an indication of the need to reduce the amount or dose of the co-enzyme antagonist/active substance (e.g. the amount of B-OT) to be administered.

The target value of enzyme inhibition is, for example and preferably, at least 20%, more preferably at least 50%, most preferably at least 70%, in each case based on the value of the original enzyme activity measured in step (1a) (as the initial value).

In the case of benfooxythiamine as co-enzyme antagonist/active ingredient, the administration is preferably oral and the amount/dose T1 of B-OT is preferably about 1 mg to about 30 mg, preferably about 2 mg to about 15 mg.

With preferably daily monitoring and, if necessary, adjustment of the amount/dose of B-OT to be administered, the target level of inhibition of enzyme activity of, for example, 50% or 70% in the patient concerned can be achieved and maintained in a relatively short time.

In general, the (amount of) single doses for patients is preferably and generally a value from the range of about 0.1 mg to about 80 mg particularly preferably a value from the range of about 1 mg to about 50 mg, each based on a body weight of 60 kg.

The invention is explained in more detail below with reference to examples of embodiments with figures. In the figures show:

On the x-axis the time is indicated in hours (h=hours)

(a) Change in individual plasma concentrations on day 1 after administration of a single dose of B-OT in an amount of 1 mg/kg/day.

The symbols mean:
— ◊ —=dog no. 3001
— □ —=dog no. 3002

(b) Change in individual plasma concentrations on day 1 after administration of a single dose of B-OT in an amount of 0.5 mg/kg/day.

The symbols mean:
— Δ —=dog no. 4001
— ○ —=dog no. 4002

(c) Change in individual plasma concentrations at day 7 after seven days of administration of single doses of B-OT in an amount of 0.5 mg/kg/day.

The symbols mean:
— Δ —=dog no. 4001
— ○ —=dog no. 3002

(d) Change in mean plasma concentrations on day 1 after administration of a single dose of B-OT at 1 mg/kg/day, and on day 1 and day 7 after daily administration of single doses of B-OT in an amount of 0.5 mg/kg/day.

The symbols mean:
— □ —=group 3, 1.0 mg/kg/day, day 1
— Δ —=Group 4, 0.5 mg/kg/day, day 1.
— ○ —=group 4, 0.5 mg/kg/day, day 7.

Figure 2:
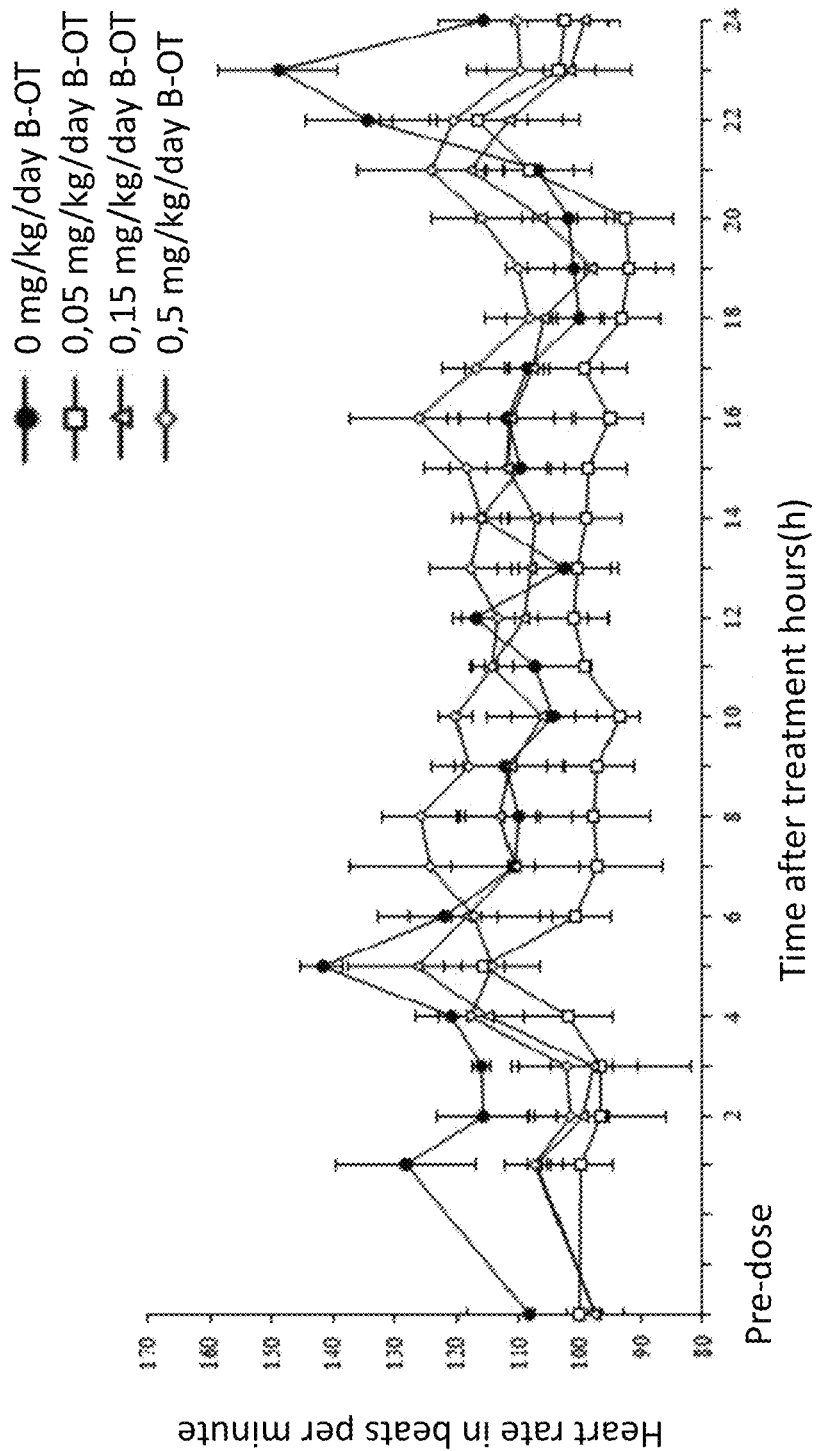

FIG. 2: Graph showing the change in plus beat with time in dogs after administration of different amounts (doses) of B-OT. On the y-axis, the pulse beat (heart rate) is given in beats per minute (bpm). On the x-axis, the time is given in hours.

The symbols mean:
— ● —=0 mg/kg/day—Benfooxythiamine=0 mg/kg/day—B-OT
— □ —=0.05 mg/kg/day—Benfooxythiamine=0.05 mg/kg/day—B-OT
— Δ —=0.15 mg/kg/day—Benfooxythiamine=0.15 mg/kg/day—B-OT
– ◊ —=0.5 mg/kg/day—Benfooxythiamine=0.5 mg/kg/day—B-OT FIG. 3: Computed tomographic image of the lungs of patient 1 before and after B-OT treatment. A: before B-OT treatment, distinct areas of viral pneumonia infiltrates are visible. B: marked decrease in infiltrates after 7 days of B-OT therapy.

FIG. 4: Computed tomographic image of the lungs of patient 2 before and after B-OT treatment. A: distinct areas of viral pneumonia infiltrates are visible before B-OT treatment. B: marked decrease of infiltrates after 7 days of B-OT treatment.

FIG. 5: Computed tomographic image of the lungs of patient 3 before and after B-OT treatment. A: before B-OT treatment, distinct areas of viral pneumonia infiltrates are visible. B: marked decrease in infiltrates after 7 days of B-OT therapy.

FIG. 6: Computed tomographic image of the lungs of patient 4 before and after B-OT treatment. A and C: distinct areas of viral pneumonia infiltrates are visible before B-OT treatment. B and D: marked decrease in infiltrates after 7 days of B-OT therapy.

FIG. 7: Computed tomography of the lungs of patient 2 (see FIG. 4) one month after the end of therapy.

BRIEF DESCRIPTION OF VARIOUS AND PREFERRED EMBODIMENTS

EXAMPLE 1: DETERMINING APPROPRIATE DOSAGES FOR THE DOSING REGIMEN AND MONITORING OF THERAPY

The determination of appropriate dosages for the dosing regimen and monitoring of therapy is described here using benfooxythiamine (B-OT) as an example.

The effect of B-OT in the patient's body is influenced by various patient-specific factors such as gene variants, binding affinity of thiamine or B-OT to the respective thiamine-dependent enzymes, active uptake and transport of thiamine by transport systems in the body, and enzymatic degradation of thiamine. The desired or optimal amount of dosage of B-OT for a particular patient or group of patients and suitable for the individual situation of the patient(s) can be determined using various diagnostic procedures and parameters.

One possible method is to measure and monitor the pulse rate and pulse rate change in the patient(s) in question.

By slowing down (throttling) the metabolism, GSSV also causes a reduction in the energy released with it. The body attempts to compensate for the lower energy release by increasing the pulse rate in order to transport more oxygen into the body so that more energy can be released as a result. The increase in the patient's pulse beat is an indication and a suitable parameter that GSSV has inhibited energy release and to what extent. If there is a sharp increase in pulse rate, e.g., in a person a pulse rate above 90, countermeasures may be necessary to increase energy release again. This can be achieved by reducing the amounts of B-OT that continue to be administered (dose reduction) or by administering thiamine (especially the thiamine form benfotiamine) FIG. 2 shows the significant increase in pulse beat (heart rate) over 24 hours in dogs after administration of various amounts of B-OT.

Another possible method is the determination of transketolase enzyme activity in lysates of erythrocytes from the patient and use of the determined transketolase enzyme activity values as a diagnostic marker for monitoring B-OT therapy. Here, basal transketolase enzyme activity in erythrocytes is the preferred parameter.

The performance of assay procedures for the determination of transketolase enzyme activity in erythrocyte lysates is known in the prior art, for example from Smeets et al., 1971 and Takeuchi et al., 1984 and Michalak et al., 2013.

Here in the example and preferably prior to the start of administration of B-OT, transketolase enzyme activity is determined in lysates of erythrocytes from the patient(s). After administration of B-OT, transketolase enzyme activity is again determined on the following day in freshly obtained lysates of erythrocytes from the patient(s) in question. Also on (all) other days after further administrations of B-OT, the transketolase enzyme activity should be determined in freshly obtained lysates of erythrocytes of the respective patient(s). By comparing the determined transketolase enzyme activity values under B-OT therapy with the determined values before the start of B-OT administration, the extent of inhibition of transketolase enzyme activity in the erythrocytes is determined. This makes it possible to select the amount (dose) of B-OT to be administered so that the desired degree of inhibition of transketolase enzyme activity and that of other thiamine-dependent enzymes is achieved.

For example, 50% inhibition may be chosen to administer B-OT in the long term to permanently inhibit inflammation.

For example, 80% inhibition may be selected if B-OT is to be administered for approximately one month and daily to achieve inhibition of metastasis in cancer patients with very advanced disease.

For monitoring B-OT therapy, measurements of one or more of the following biochemical markers in the blood of patients can also be used:

Increase in bilirubin level, increase in ALAT (alanine aminotransferase) and ASAT (aspartate aminotransferase) enzymes, decrease in CK (creatine kinase) enzyme, decrease in protein concentration (not albumin level), decrease in white and red blood cells, increase in platelets (thrombocytes), decrease in reticulocytes.

EXAMPLE 2: USE ACCORDING TO THE INVENTION OF THE ACTIVE SUBSTANCE BENFO-OXYTHIAMINE "B-OT" FOR GSSV IN CANCER CELLS CIRCULATING IN THE BLOOD

Cancer cells circulating in the patient's blood are detected and separated and isolated from the blood. Detection, separation and isolation are preferably performed without the use of surface markers, i.e., for example, by means of cell sorting and multi-staining single-cell analysis "MSSCA", so that the isolated cancer cells are a representative image of the malignancy (cancer tumor) in the patient.

These isolated cancer cells are treated in a test series "A" with the cancer therapeutic agent(s) under consideration, and in a parallel test series "B" first incubated with the agent benfo-oxythiamine ("B-OT")—as a preferred example of an inhibitory thiamine analogue or an inhibitory co-enzyme antagonist—and subsequently treated with the cancer therapeutic agents from test series A (see also Example 3). The results from both test series A and B are compared, and in particular if it is determined that a preferred cancer therapeutic agent (or its active ingredient) from test series A appears to be ineffective or inadequately effective according to guidelines or for other reasons, but in contrast shows a satisfactory effect after pretreatment with B-OT according to the result in test series B, pretreatment with B-OT is indicated as a co-therapy of the actual established cancer therapy in the patient's upcoming cancer therapy. Regarding the duration and intensity of pretreatment or co-treatment with B-OT, experimental studies have shown that a two-day treatment immediately prior to application to concurrent co-therapy with the actual established cancer therapy is promising and thus appropriate.

EXAMPLE 3: DETERMINATION OF THE APPROPRIATE COMBINATION OF EFFECT OF GSSV ACCORDING TO THE INVENTION (GSSV THERAPY) AS PRE- OR CO-THERAPY AND SUBSEQUENT OR CONCURRENT DRUG THERAPY (E.G. CHEMOTHERAPY AND/OR TARGETED CANCER THERAPY) AND/OR RADIOTHERAPY IN A CANCER PATIENT

A suitable combination of (i) the application of a co-enzyme antagonist according to the invention and the GSSV thereby induced (GSSV therapy)—preferably using at least one inhibitory thiamine analogue (in particular oxythiamine, benfo-oxythiamine ("B-OT") and/or a benfo-oxythiamine analogue)—as pre- or co-therapy (initiation of the administration of B-OT prior to or concurrently with or after the initiation of the established cancer therapy of the cancer patient in question) and (ii) the application of therapeutics (agents, drugs) that act in a non-directed manner (e.g., cisplatin) or targeted (e.g., sorafenib, imatinib, Erbitux, Avastin, Herceptin) and/or the application of radiotherapy (according to current evidence-based therapy rules) is ascertainable in different ways:

a) The cancer patient is initially treated with established chemotherapy (using classical cytostatics, i.e. cell type non-specific cell proliferation inhibitors) and/or targeted cancer therapy (using cell type specific agents such as sorafenib and others) and/or radiotherapy (according to current evidence-based therapy rules). If his tumor cells (a subset thereof or all of them) either already show resistance to the therapy or have developed resistance under the therapy, he will be further treated with a combined therapy comprising the administration of the co-enzyme antagonist according to the invention as active ingredient (drug) and the application of the established chemotherapy and/or targeted cancer therapy and/or radiotherapy. (b) Cancer cells are taken from a cancer patient who has not yet received established chemotherapy and/or targeted cancer therapy and/or radiation therapy and treated in vitro, preferably ex vivo (i.e., on a malignancy tissue sample freshly isolated from the organism), with the cancer therapeutic agents under consideration to determine which agent or combination of agents works best. In this way, a chemotherapeutic agent or targeted cancer therapeutic agent or radiation therapeutic agent or a combination of several of these therapeutic agents can be identified that is effective in the cancer patient's individual situation. This will also determine whether resistance to the therapeutics used is present in the malignancy cells in question.

Parallel to this in vitro test series "A" of the cancer therapeutics under consideration per se, a test series "B" and/or a test series "C" is carried out. In test series B, the melanoma cells of the patient are first pretreated with a co-enzyme antagonist according to the invention as active substance (drug), —for example and preferably with an inhibitory thiamine analogue—, and then treated with the planned cancer therapeutic agent.

In test series C, the patient's malignant cells are treated simultaneously with both a co-enzyme antagonist according to the invention as active ingredient (drug), —for example and preferably with an inhibitory thiamine analogue —, and with the planned cancer therapeutic agent.

By comparing the results from test series A with the results from test series B and test series C, it can be determined whether a targeted cancer therapy will be effective or more effective by combining it with a drug according to the invention in the course of a pre-treatment (as in test series A) or in the course of a co-therapy (as in test series B, i.e. with parallel, approximately simultaneous administration of the drug according to the invention and the conventional cancer therapeutic) than alone (i.e. without this pre-treatment).

This procedure (b) has in particular the advantage that the time interval, within which any resistance of the cancer cells of the patient concerned to the chemotherapeutic and/or radiotherapeutic agent intended for use develops or existing resistance is detected, is considerably reduced. In other words, on the one hand, the interval between the formation of resistance and the time of detection of this resistance formation can be massively shortened, because the resistance of the cancer cells to the therapeutic agent in question can be determined directly ex vivo, and does not have to be determined indirectly and in vivo on the basis of surrogate markers such as cancer tumor markers or visualization of the size of the cancer tumor (malignancy), as has been the case to date. On the other hand, already existing resistances can be detected before therapy. Thus, statements can be made as to whether a specific chemotherapeutic agent (i.e., a cell-type non-specific cell proliferation inhibitor such as the classical cytostatics and/or a cell-type specific agent such as sorafenib) and/or radiotherapeutic agent can be used in a meaningful and promising manner. This enables a targeted therapy oriented to the individual situation of the cancer patient with the best possible success of the therapy. This opens up far-reaching perspectives, particularly with regard to individualized medicine.

EXAMPLE 4: STUDY IN DOGS ON THE CONVERSION OF BENFO-OXYTHIAMINE "B-OT" TO OXYTHIAMINE "OT" IN THE ORGANISM

Male and female dogs (Beagle breed) were administered B-OT (benfo-oxythiamine) orally once daily for periods of one to seven days in amounts of 1 mg/kg/day or 0.5 mg/kg/day.

The toxicokinetics of the active metabolite OT (oxythiamine) was determined in plasma samples obtained on the first day "Day 1" and on the seventh day "Day 7" after the start of administration. The measurement results obtained are shown graphically in FIGS. 1 (a) to (d).

Figure 1A:
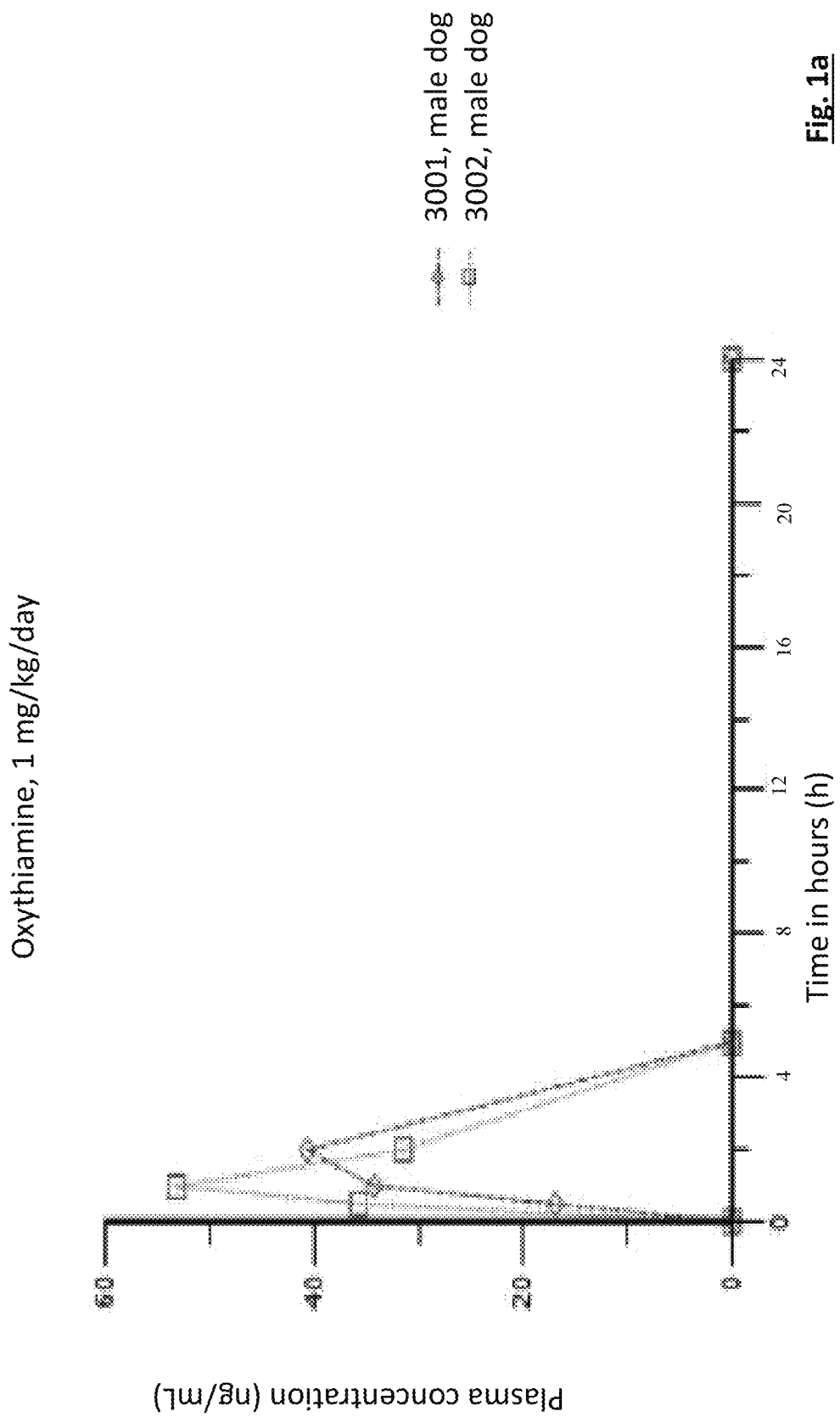
FIG. 1: Change in individual plasma concentrations of OT with time (over 24 hours) in male beagle dogs. The y-axis indicates—the plasma concentration in ng/ml.

FIG. 1a shows the changes in individual plasma concentrations of oxythiamine (OT) with time in male beagle dogs on day 1, i.e., the first day after administration of a single dose of B-OT in an amount of 1 mg/kg/day.

Figure 1B:
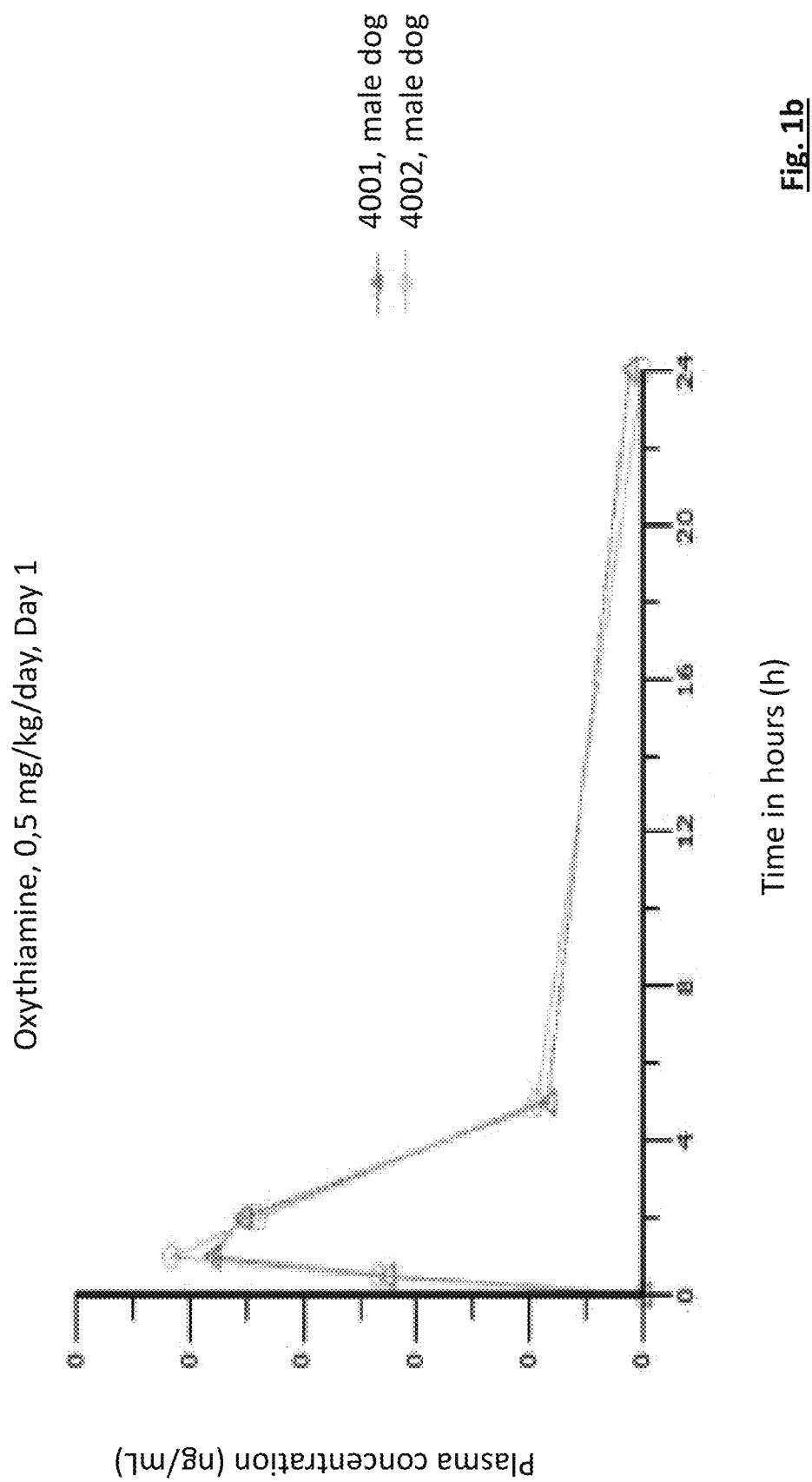
Figure 1C:
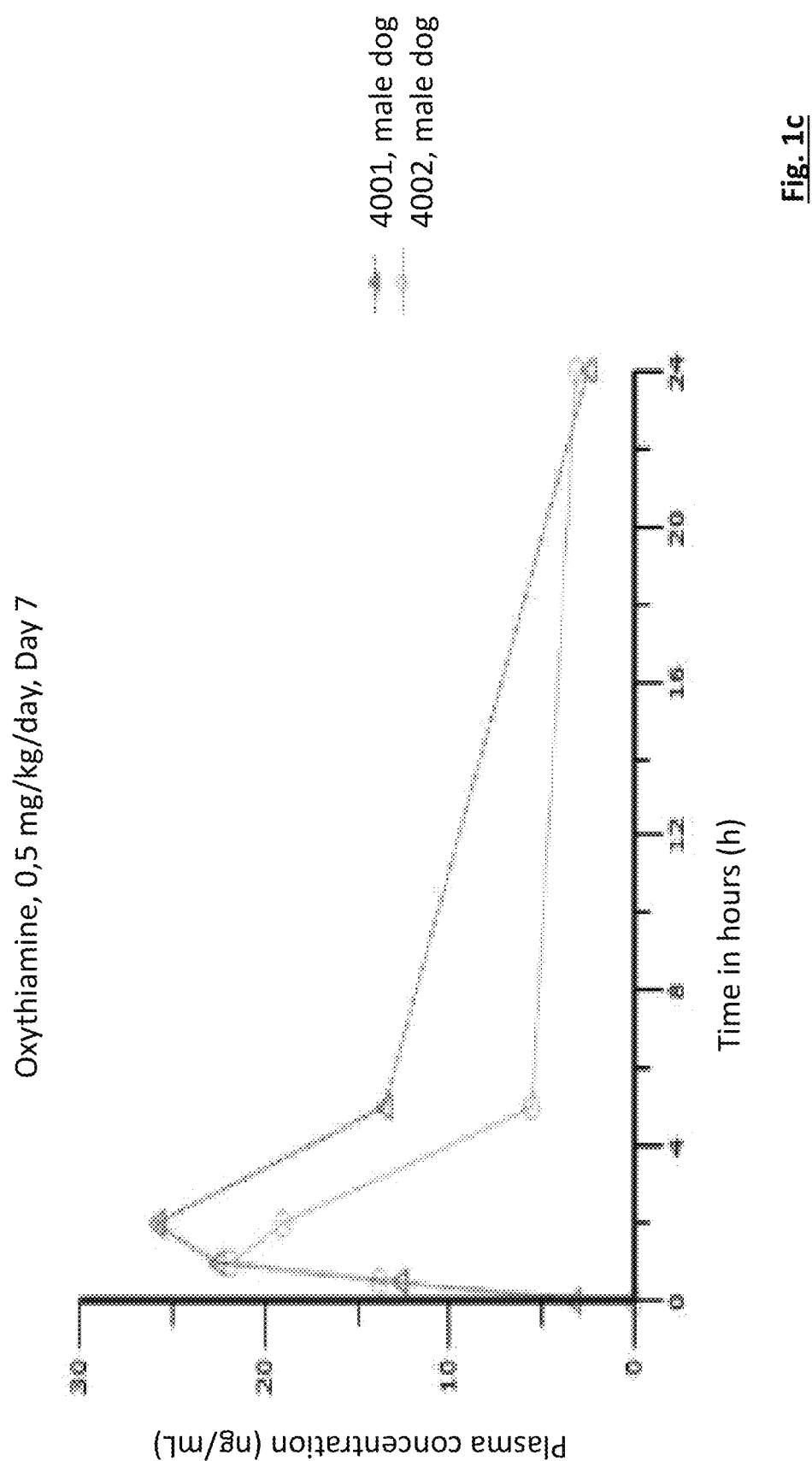

FIG. 1b and FIG. 1c show the changes in individual plasma concentrations of oxythiamine (OT) with time in male beagle dogs on day 1, i.e., on the first day (FIG. 1b) and day 7, i.e., on the seventh day (FIG. 1c) of daily administration of single doses of B-OT in an amount of 0.5 mg/kg/day.

Figure 1D:
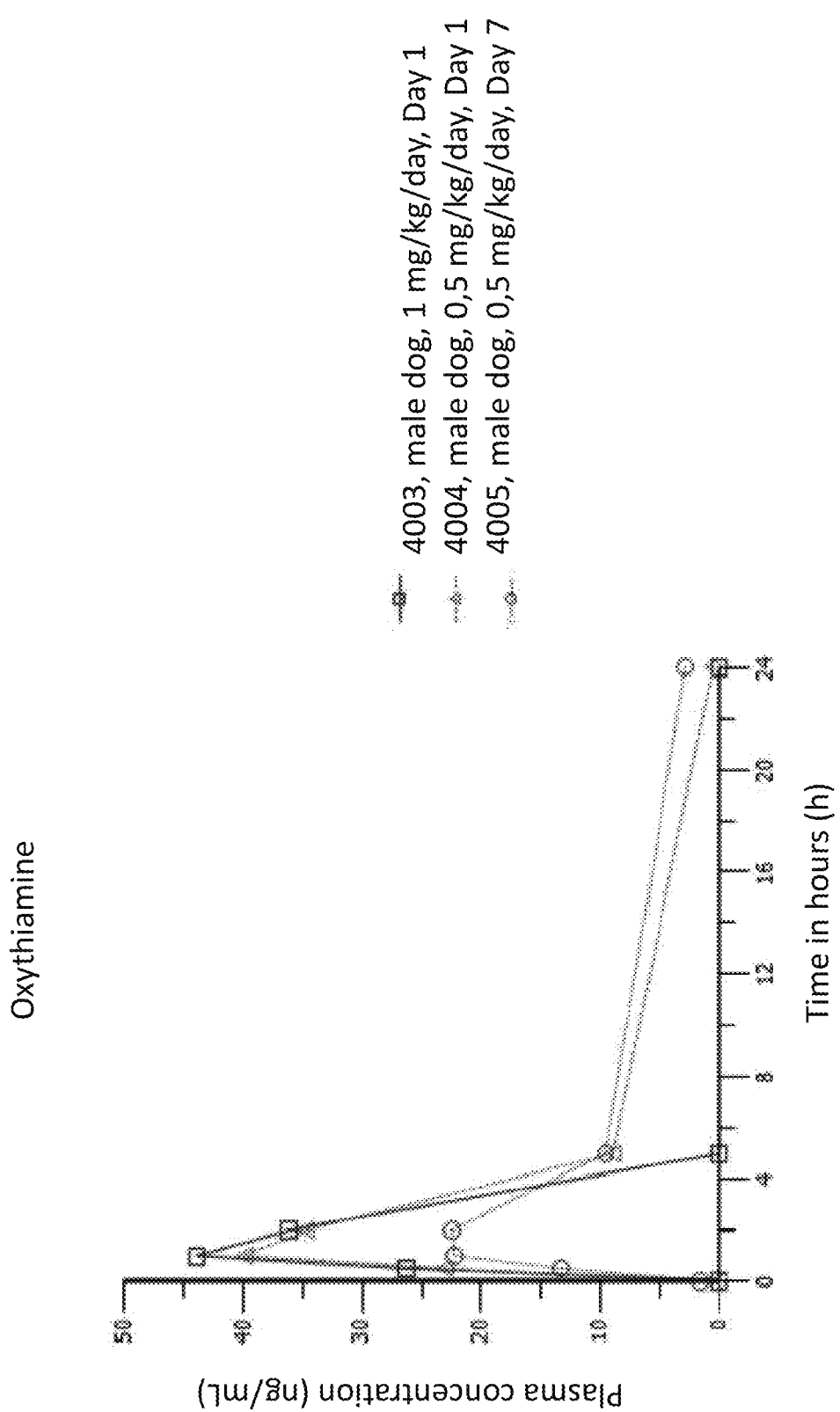

FIG. 1d shows the changes in mean (averaged) plasma concentrations of oxythiamine (OT) with time in the male beagle dogs (of FIGS. 1a to 1c) on day 1 and day 7 during daily administration of single doses of B-OT at a concentration of 0.5 mg/kg/day and on day 1 after administration of a single dose of B-OT in an amount of 1.0 mg/kg/day.

Oxythiamine was not found in plasma samples obtained on day 1 before administration of B-OT. Systemic exposure with respect to OT was achieved in all animals treated with B-OT. For all applied doses of B-OT, the time of maximum OT plasma concentration (Tmax) after administration of B-OT was investigated, with the highest value obtained between one and two hours. With a stepwise increase in the applied B-OT dose from 0.2 mg/kg to 1.0 mg/kg, an increase in plasma concentrations of oxythiamine (OT) was observed that was approximately linearly proportional to the increase in dose.

After oral administration of B-OT single doses and based on a dose-normalized C max and partial AUC (area under the curve) values, a less than dose-proportional increase in plasma OT was observed in male beagle dogs over the range of applied doses of B-OT.

Treatment of the dogs with B-OT was well tolerated. No relevant abnormalities in the behavior or relevant changes in the physical condition of the dogs were observed throughout the study period, in particular no significant variations in body weight. The animals were exposed to the active metabolite OT but not to the preform (prodrug) B-OT.

EXAMPLE 5: ADMINISTRATION OF B-OT TO PATIENTS WITH SARS-COV-2 INFECTION

In the context of curative trials, four patients who had been diagnosed with covid-19 pneumonia requiring inpatient treatment were selected from a total collective of over 700 patients with covid-19 disease requiring inpatient treatment. Based on laboratory data and previous disease course, these patients were expected to have a severe course of COVID-19 disease and were therefore treated at the same treatment center with the current standard therapy, namely dexamethasone, anticoagulation, and oxygen therapy. In addition to the standard therapy, these four patients were treated with B-OT administration, i.e. they received 6 mg B-OT per day perorally for seven days.

Under this additional therapy with B-OT, none of the four patients required intensive care. None of the patients showed side effects that could be attributed to the administration of B-OT.

At the start of B-OT treatment, all patients had SARS-CoV-2-related pneumonia. The severe damage to the lungs was documented by computed tomography (CT). These CT images of the lungs show marked infiltrates due to viral pneumonia (see FIG. 3A-FIG. 6A).

A repeat imaging examination of the lungs by computed tomography at the end of the seven-day B-OT therapy documents the rapid healing process and shows a significant decrease in the previously pronounced infiltrates (see FIG. 3B—FIG. 6B).

For one patient (patient 2), a computed tomographic image of the lungs obtained during follow-up is available one month after the end of therapy, and it shows stable findings (FIG. 7).

In contrast to the overall collective of more than 700 patients, none of the four patients receiving additional therapy with B-OT, despite the initial severity of respiratory distress, required intensive care or respiratory support therapy beyond nasal cannula or mask oxygen insufflation, such as non-invasive or invasive ventilation, during the course of the disease.

In all patients with additional B-OT therapy, a significant reduction of the inflammatory parameters C-reactive Protein (CRP) and Interleukin-6 (IL-6) was also observed (see Table 1). The clinical levels of these immunoinflammatory markers represent important parameters for assessing the severity of the disease. High levels of the proinflammatory cytokine IL-6 and/or of C-reactive protein (CRP) indicate severe disease and a high-risk disease course.

The proinflammatory cytokine IL-6 with pleiotropic properties also appears to play a key role in the "cytokine storm" also described for patients with SARS-CoV-2 infections. Its constitutive expression causes organ damage and severe pain.

In all patients with additional B-OT therapy, the required inpatient stay was significantly shorter compared with the overall collective of more than 700 patients, on average one week less.

CITED NON-PATENT LITERATURE

Smeets E H, Muller H, de Wael J (July 1971): 'A NADH-dependent transketolase assay in erythrocyte hemolysates'. Clin. Chim. Acta. 33 (2): 379-86. doi:10.1016/0009-8981(71)90496-7. hdl:1.874/24761. PMID 4330339.

Takeuchi T, Nishino K, Itokawa Y: Improved determination of transketolase activity in erythrocytes, Clinical Chemistry, Vol. 30, Issue 5, 1 May 1984, Pages 658-661. https://doi.org/10.1093/clinchem/30.5.658

Michalak S, Michalowska-Wender G, Adamcewicz G, Wender M B: Erythrocyte transketolase activity in patients with diabetic and alcoholic neuropathies. Folia Neuropathol 2013; 51(3):222-226. https://doi: 10.5114/fn.2013.37706.

The invention claimed is:

1. A method for successively slowing anabolic, catabolic and/or energy-releasing metabolic processes of cells in the body of a patient suffering from cancer comprising:
   administering as part of a tumor cell treatment of the patient suffering from cancer oxythiamine (OT) or benfooxythiamine (B-OT), wherein the OT or B-OT is administered in an amount effective to inhibit a thiamine-dependent enzyme to a target value, wherein the target value corresponds to an inhibition of an activity of the thiamine-dependent enzyme by at least 20% in the cells in the body of the patient, wherein the cells comprise healthy and tumor cells of the patient, wherein the administration comprises:
   (i) administering the OT or B-OT in a first dose of a dosage regime,
   (ii) subsequently monitoring an effect of the inhibition on the healthy cells of the patient,
   (iii) adjusting, if desired, the target value based on (ii) and
   (iv) administering in one or more consecutive doses of the dosage regime, the OT or B-OT in an amount effective to reach the target value of (iii) without irreversibly damaging the healthy cells of the patient and/or while maintaining basic functions of the body of the patient, and
   (v) subsequently or concurrently administering a chemotherapy, radiotherapy and/or targeted cancer therapy to the patient.

2. The method of claim 1, wherein the enzyme is inhibited by at least 50%.

3. The method of claim 2, wherein benfo-oxythiamine is administered.

4. The method of claim 1, wherein
   the effect of the inhibition on the healthy cells of the patient is measured via a number of heart beats per minute of the patient.

5. The method of claim 1, wherein the thiamine-dependent enzyme is a transketolase.

6. The method of claim 1, wherein the OT or B-OT is administered to the patient as a pretreatment prior to the chemotherapy, radiotherapy and/or targeted cancer therapy.

7. The method of claim 1, wherein the OT or B-OT is administered orally according to a dosage regimen in which individual doses, for patients having 60 kg body weight, range from about 0.1 mg to about 80 mg, wherein the patient has an actual body weight and the individual doses are adjusted according to the actual body weight of the patient based on the doses for patients having the 60 kg body weight.

8. The method of claim 7, wherein the individual doses, for the patients having 60 kg body weight, range from about 1 mg to about 50 mg.

9. The method of claim 1, wherein the OT or B-OT is administered to the patient suffering from cancer in a continuous therapy lasting weeks or months, and is administered according to the dosage regimen determined by a method comprising:

(1) on day 1:
(1a) measurement of the enzyme activity of the thiamine-dependent enzyme-in a first body fluid sample I of the patient,
(1b) subsequent administration of the OT or B-OT to the patient in an amount T1 to inhibit an initial enzyme activity of the thiamine-dependent enzyme to the a-target value;
(2) on day 2:
(2a) measurement of enzyme activity of the thiamine-dependent enzyme in a body fluid sample II of the patient obtained on that day;
(2b) comparison of the enzyme activities measured in body fluid sample I and body fluid sample II and calculation of the inhibition of the activity of the thiamine-dependent enzyme;
(2c) subsequently administering the OT or B-OT to the patient in an amount T2, wherein T2=T1, T2>T1 or T2<T1 and wherein the amount T2 is determined based on the calculation in 2(b);
(3) on day 3 and subsequent days, (i), until the target value of enzyme activity inhibition is reached:
repeating (2a), 2b) and (2c) wherein the OT or B-OT is administered to the patient in an amount T(i), which is determined analogous to the amount T2 in (2c).

10. The method of claim 9, wherein the target value of enzyme inhibition of the thiamine-dependent enzyme is at least 70%, based on the value of the original enzyme activity of the thiamine-dependent enzyme measured in (1a).

11. The method of claim 9, wherein benfooxythiamine (B-OT) is administered, and the amount T1 of B-OT is 1 mg to 30 mg and that the administration of B-OT is oral.

12. The method of claim 11, wherein the amount T1 of B-OT is 2 mg to 15 mg.

13. The method of claim 8, wherein B-OT is administered orally and, based on patients having a body weight of 60 kg, in the following doses
(a) when used in combination with radiotherapy:
on the day of radiotherapy before radiotherapy once at about 1-150 mg, about 10-75 mg, or about 30-50 mg,
on the day after radiotherapy once at about 1-70 mg, about 3-40 mg, or about 4-20 mg, and
on the second day after radiotherapy once at about 1-40 mg, about 3-25 mg, or about 4-18 mg;
(b) when used in combination with chemotherapy:
on the day before chemotherapy once at about 1-150 mg, about 10-75 mg, or about 30-50 mg,
on the day of chemotherapy once at about 1-150 mg, about 10-75 mg, or about 5-50 mg, and
on the day after chemotherapy once at about 1-100 mg, about 10-75 mg, or about 5-50 mg;
(c) when used in combination with one, or more, targeted cancer therapies using imatinib and/or sorafenib and/or erbitux and/or avastin and/or gemcitabine and/or another anti-cancer drug:
on the day before chemotherapy once at about 1-100 mg, about 10-75 mg, or about 5-50 mg,
on the day of chemotherapy once at about 1-100 mg, about 10-75 mg, or about 5-50 mg, and
on the day after chemotherapy once at about 1-100 mg, about 10-75 mg, or about 5-50 mg; or
(d) when used as monotherapy or in combination with one or more other therapies, where the application lasts longer than one week, than two weeks, longer than three weeks or longer than four weeks:
per day about 1-30 mg, about 2-15 mg, or about 3-10 mg, and in each case as a single dose or in the form of several partial doses,
wherein the patient has an actual body weight and the doses recited in a) to d) are adjusted according to the actual body weight of the patient based on the doses for the patients having the body weight of 60 kg.

14. The method of claim 1, comprising a treatment phase with the dosage regimen, wherein following the treatment phase, the metabolism of the healthy cells reactivates.

15. A method for successively slowing anabolic, catabolic and/or energy-releasing metabolic processes of cells in a body of a patient suffering from cancer comprising:
administering, as part of a tumor cell treatment of the patient suffering from cancer oxythiamine (OT) or benfooxythiamine (B-OT), wherein the OT or B-OT is administered in an amount effective to inhibit a thiamine-dependent enzyme to a target value, wherein the target value corresponds to an inhibition of an activity of the thiamine-dependent enzyme by at least 20% in the cells in the body of the patient, wherein the cells comprise healthy and tumor cells of the patient and wherein the administration comprises:
(i) administering the OT or B-OT in a first dose of a dosage regime,
(ii) adjusting, if desired, the target value and
(iii) administering in one or more consecutive doses of the dosage regime, the OT or B-OT in an amount effective to reach the target value of (ii) without irreversibly damaging the healthy cells of the patient, wherein
the administering results in a slowing of the patient's metabolism, without causing irreversible cell and tissue damage in the patient, and
(iv) subsequently or concurrently administering a chemotherapy, radiotherapy and/or targeted cancer therapy to the patient.

16. The method of claim 15, wherein B-OT is administered.

17. The method of claim 1, wherein the inhibition of the activity of the thiamine-dependent enzyme does not cause irreversible cell and tissue damage in the patient.

18. The method of claim 15, wherein the OT or B-OT is administered in an amount effective to inhibit a thiamine-dependent enzyme to a target value, wherein the target value corresponds to an inhibition of an activity of the thiamine-dependent enzyme by at least 70%.

* * * * *

UNITED STATES PATENT AND TRADEMARK OFFICE
CERTIFICATE OF CORRECTION

PATENT NO. : 12,168,010 B2
APPLICATION NO. : 18/010816
DATED : December 17, 2024
INVENTOR(S) : Coy et al.

Page 1 of 1

It is certified that error appears in the above-identified patent and that said Letters Patent is hereby corrected as shown below:

In the Specification

In Column 1, Line 9, delete "DE 0 2020 116 980.9," and insert -- DE 10 2020 116 980.9, --, therefor.

In Column 2, Line 45, delete "e g" and insert -- e. g. --, therefor.

In Column 8, Line 11, delete "oxythiamine" and insert -- oxythiamine. --, therefor.

In Column 9, Line 2, delete "humans)" and insert -- humans). --, therefor.

In Column 12, Line 32, delete "manner" and insert -- manner. --, therefor.

In Column 13, Line 44, delete "(relapses9." and insert -- (relapses). --, therefor.

In Column 21, Line 45, delete "Hoff s" and insert -- Hoff's --, therefor.

In Column 24, Line 38, delete "—●=0" and insert -- –●– = 0 --, therefor.

In Column 27, Line 38, delete "melanoma" and insert -- malignoma --, therefor.

In Column 30, Line 2, delete "hdl:1.874/24761." and insert -- hdl:1874/24761. --, therefor.

In the Claims

In Column 31, in Claim 9, Lines 10-11, delete "a-target" and insert -- target --, therefor.

In Column 31, in Claim 11, Line 35, delete "that the" and insert -- the --, therefor.

Signed and Sealed this
Thirteenth Day of May, 2025

Coke Morgan Stewart
*Acting Director of the United States Patent and Trademark Office*